US012734121B2

(12) United States Patent
Starkulla

(10) Patent No.: US 12,734,121 B2
(45) Date of Patent: Sep. 15, 2026

(54) ESTOLIDE ESTERS FOR THE COSMETIC TREATMENT OF SKIN

(71) Applicant: Clariant International Ltd., Muttenz (CH)

(72) Inventor: Gundula Starkulla, North Salem, NY (US)

(73) Assignee: CLARIANT INTERNATIONAL LTD, Muttenz (CH)

(*) Notice: Subject to any disclaimer, the term of this patent is extended or adjusted under 35 U.S.C. 154(b) by 483 days.

(21) Appl. No.: 18/265,563

(22) PCT Filed: Dec. 7, 2021

(86) PCT No.: PCT/EP2021/084556

§ 371 (c)(1),
(2) Date: Jun. 6, 2023

(87) PCT Pub. No.: WO2022/122719

PCT Pub. Date: Jun. 16, 2022

(65) Prior Publication Data

US 2024/0148625 A1 May 9, 2024

(30) Foreign Application Priority Data

Dec. 7, 2020 (EP) .................................... 20212306

(51) Int. Cl.

| | |
|---|---|
| ***A61K 8/37*** | (2006.01) |
| ***A61Q 17/04*** | (2006.01) |
| ***A61Q 19/00*** | (2006.01) |

(52) U.S. Cl.

CPC ................ *A61K 8/37* (2013.01); *A61Q 17/04* (2013.01); *A61Q 19/007* (2013.01)

(58) Field of Classification Search

CPC ............. A61K 8/37; A61K 8/85; A61Q 19/00
See application file for complete search history.

(56) References Cited

U.S. PATENT DOCUMENTS

| | | | | |
|---|---|---|---|---|
| 4,428,850 | A | 1/1984 | Zoleski | |
| 2013/0065970 | A1 | 3/2013 | Bredsguard | |
| 2015/0045430 | A1* | 2/2015 | Parson | A61Q 19/00 554/1 |
| 2018/0125767 | A1* | 5/2018 | Benson | A61Q 5/02 |
| 2020/0261336 | A1 | 8/2020 | Consoli | |

FOREIGN PATENT DOCUMENTS

| | | | |
|---|---|---|---|
| WO | 2008055692 | | 5/2008 |
| WO | 2014078149 | A1 | 5/2014 |
| WO | 2016174256 | A1 | 11/2016 |
| WO | 2017163182 | A2 | 9/2017 |

OTHER PUBLICATIONS

International Search Report issued in App. No. PCT/EP2021/084556, dated Feb. 22, 2022, 2 pages.

* cited by examiner

*Primary Examiner* — Mark V Stevens

(57) ABSTRACT

The invention relates to the use of a cosmetic composition comprising at least one compound according to Formula (1)

Formula (1)

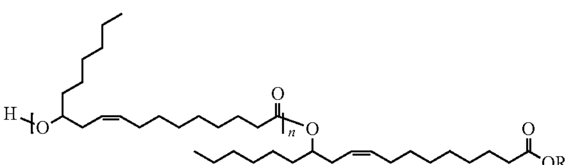

wherein
R is selected from linear or branched C3-C20-alkyl; and
n is selected from 1 to 20;
for the cosmetic treatment of skin.

16 Claims, No Drawings

ESTOLIDE ESTERS FOR THE COSMETIC TREATMENT OF SKIN

The invention relates to the use of a cosmetic composition comprising at least one compound according to Formula (1) as defined herein for the cosmetic treatment of skin, to a method for the cosmetic treatment of skin, and to the use of at least one compound according to Formula (1) as defined herein as skin conditioner (e.g. emollient, lubricant, moisturizer, refatting agent, smoothing agent, soothing agent), dispersing agent, wetting agent, film former, emulsion stabilizer, binding agent, or antifoaming agent in a cosmetic composition.

The skin is the largest organ of the human organism. The skin mainly intends to protect human beings against environmental aggressions, but it also supports other essential functions such as permeation, metabolism, and thermoregulation, and it actively contributes to the sensorial function.

The skin is made of a complex, layered structure of which the stratum corneum, the horny layer, is the outermost protective barrier of the skin. The stratum corneum is responsible for the retention of water and the hydration balance in the superficial skin layers, it controls the transport of water and other compounds into and out of the skin, and it is covered with a hydrolipidic protective film. The function of the epidermis is only ensured when the stratum corneum is properly moisturized and the hydrolipidic film is healthy and balanced.

Therefore, there is a huge need for effective skin conditioning agents which support an ideal environment for all the functions of a healthy epidermis.

There still is a great need for improved cosmetic compositions, in particular for skin treatments, and for new skin care compositions which support not only the skin to recover from loss of natural lipids and keep it moist but which also fulfill the high standards of challenging formulations and great demands for appealing textures and sensorial experiences.

Moisturization is the most basic consumer expectation of a cosmetic skin care emulsion and therefore the most common functional cosmetic claim. But besides proven skin hydration benefits, there is also a need for skin conditioning agents which significantly enhance the skin barrier function, reduce the skin roughness and improve the skin elasticity.

Additionally, cosmetic formulators are dealing with more and more challenging formulations as consumers are expecting products with multiple benefits. Hence, new multifunctional skin conditioning ingredients are required to solve technical formulation challenges like organic UV filter or fragrance solubilization, pigment wetting and inorganic UV filter dispersion. At the same time these ingredients must be applicable across a broad pH range, stable to hydrolysis, stable against oxidation, compatible with other ingredients, especially with lipophilic ingredients, and must contribute to the formulation stability as well as to the formulation aesthetics.

One of the core challenges for formulators is to master the hydration of the stratum corneum as well as the technical formulation requirements and at the same time balance the sensory experience during use of the cosmetic product. Therefore, skin conditioning agents with specific sensory attributes are highly desired. The unique combination of an ingredient's molecular weight, its polarity, and its viscosity are determining "the skin feel" which is a combination of lubricity, spreadability, absorption into the skin and duration on the skin surface.

Furthermore, there is a need for providing components for cosmetic compositions that are based on natural and renewable materials or derived therefrom. Indeed, consumers are, in present times, highly conscious as to the source of the components used in such compositions, and these consumers feel much more comfortable using components that are derived from natural and renewable materials. One objective of the present invention is therefore to provide a stable cosmetic ingredient for skin care products based on preferably renewable starting materials, more preferably natural renewable starting materials.

General cosmetic skin treatment compositions are known, however there is still a need for compositions designed for skin care, which are based on natural and renewable materials or derived therefrom. It now was found that specific types of estolide ester compounds are excellent components for cosmetic compositions, in particular for skin treatment.

The invention relates to the use of a cosmetic composition comprising at least one compound according to Formula (1)

Formula (1)

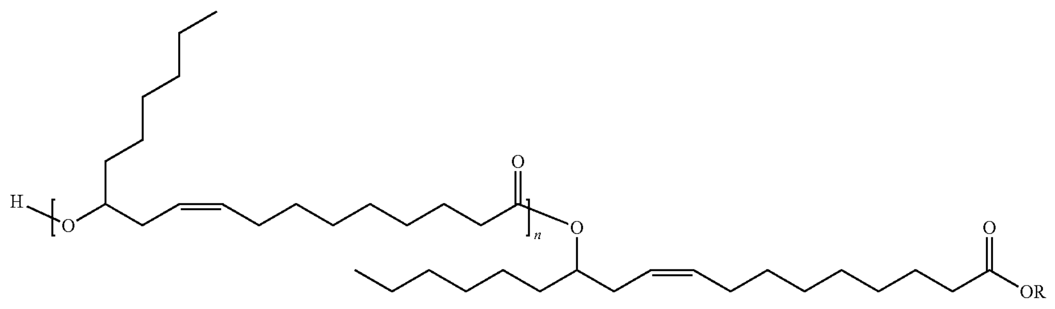

wherein

R is selected from linear or branched C3-C20-alkyl; and n is selected from 1 to 20;

for the cosmetic treatment of skin.

Advantageously, compounds of Formula (1) show when used in a cream beneficial effects on the skin. The use of compounds of Formula (1) leads to a decreased transepidermal water loss (TEWL) and thus an improved skin barrier function, as well as an improved skin hydration, an improved skin elasticity, and a reduced skin roughness resulting in an improved skin relief.

Additionally, compounds of Formula (1) show favorable properties in different application categories. The high refractive index of compounds of Formula (1) leads to an improved shine in lip applications like lip gloss, lip sticks or lip balms. Due to the high polarity and high surface tension of the compounds of Formula (1), very good wetting and dispersing of organic pigments, inorganic pigments, and physical sunscreens are achieved, resulting in an improved pay-off and color strength when used in color cosmetics or in an increased sun protecting factor when used in sunscreen applications. Furthermore, very good solubilization of crystalline UV filters and actives as well as of fragrances are achieved with the compounds of Formula (1). The high viscosity of the compounds of Formula (1) shows also good impact on the physical formulation stability and a certain thickening effect in anhydrous, oil in water, and water in oil formulations. Besides the above-mentioned benefits, compounds of Formula (1) show also good general compatibility with other lipophilic ingredients like oils, waxes, butters, and emulsifiers independent of their natural or synthetic origin. Moreover, compounds of Formula (1) are broadly applicable on the basis of their wide pH compatibility, their stability to hydrolysis, and their stability against oxidation. The high viscosity and high surface tension of the compounds of Formula (1) together with their molecular weight results in a distinctive sensory effect. Formulations with compounds of Formula (1) show improved lubricity, leave a noticeable residual film on the skin and result in a more persistent emollient skin feel. Furthermore, the compounds of Formula (1) show low spreadability on Vitro-Skin, and when formulated in a cream a more protective skin feel is achieved.

The compound according to Formula (1) is an estolide ester. As used herein, the term "estolide ester" means an oligomeric fatty acid ester, wherein the monomers are joined by ester linkages. The term "estolide ester" is known in the art.

Estolides are long-chain esters of the same or different hydroxy fatty acids or hydroxy unsaturated fatty acids. Estolide esters may be formed by esterification of an estolide with an alcohol, or directly by adding an alcohol during the synthesis of an estolide.

According to the invention, the cosmetic composition is used for the cosmetic treatment of skin. The expression "cosmetic treatment of skin" refers to a non-medical and non-therapeutic treatment.

Preferably, the cosmetic treatment of skin comprises or is selected from skin cleansing, skin moisturizing, skin softening, skin whitening, skin lightening, skin exfoliating, skin anti-aging treatment, skin anti-wrinkle treatment, skin barrier repair treatment, skin anti-acne treatment, skin anti-cellulite treatment, skin depilation, skin shaving, chemical peeling treatment, slimming treatment, skin deodorizing, anti-perspirant treatment, skin mattifying, skin firming, skin plumping, self-tanning treatment, anti-dark circle treatment, UV protection, skin soothing, anti-pollution treatment, nail cuticle treatment, after-sun treatment, and application of color cosmetics.

Also preferably, the cosmetic treatment of skin comprises or is selected from skin cleansing, skin moisturizing, skin softening, skin whitening, skin lightening, skin exfoliating, skin anti-aging treatment, skin anti-wrinkle treatment, skin anti-cellulite treatment, skin depilation, skin shaving, chemical peeling treatment, slimming treatment, skin deodorizing, anti-perspirant treatment, skin mattifying, skin firming, skin plumping, self-tanning treatment, anti-dark circle treatment, skin soothing, anti-pollution treatment, nail cuticle treatment, after-sun treatment, and application of color cosmetics.

Particularly preferably, the cosmetic treatment of skin comprises or is selected from skin moisturizing, skin softening, skin anti-aging treatment, skin anti-wrinkle treatment, skin barrier repair treatment, UV protection, skin soothing and application of color cosmetics.

Also particularly preferably, the cosmetic treatment of skin comprises or is selected from skin moisturizing, skin softening, skin anti-aging treatment, skin anti-wrinkle treatment, skin soothing and application of color cosmetics.

According to the invention, the cosmetic composition used in the present invention comprises at least one compound according to Formula (1) wherein R is selected from linear or branched C3-C20-alkyl; and n is selected from 1 to 20.

Preferably, R in Formula (1) is selected from linear or branched C6-C18-alkyl, more preferably from linear or branched C8-C18-alkyl, even more preferably from linear C10-C16-alkyl, particularly preferably from linear C12-C14-alkyl.

Preferably, n in Formula (1) is selected from 1 to 15, more preferably from 2 to 10, even more preferably from 2 to 8, particularly preferably from 3 to 7.

In preferred embodiments, R in Formula (1) is selected from linear or branched C6-C18-alkyl, and n in Formula (1) is selected from 1 to 15. In more preferred embodiments, R in Formula (1) is selected from linear or branched C8-C18-alkyl, and n in Formula (1) is selected from 2 to 10. In even more preferred embodiments, R in Formula (1) is selected from linear C10-C16-alkyl, and n in Formula (1) is selected from 2 to 8. In particularly preferred embodiments, R in Formula (1) is selected from linear C12-C14-alkyl, and n in Formula (1) is selected from 3 to 7.

According to the invention, the cosmetic composition used in the present invention comprises at least one compound according to Formula (1). The cosmetic composition used in the present invention may comprise one or more compounds according to Formula (1). The cosmetic composition used in the present invention may comprise a mixture of compounds according to Formula (1).

In particularly preferred embodiments, the cosmetic composition used in the present invention comprises at least one compound according to Formula (1) wherein R is linear or branched C12-alkyl and at least one compound according to Formula (1) wherein R is linear or branched C14-alkyl.

In particularly preferred embodiments, the cosmetic composition used in the present invention comprises at least one compound according to Formula (1) wherein R is linear C12-alkyl and at least one compound according to Formula (1) wherein R is linear C14-alkyl.

In preferred embodiments, the cosmetic composition used in the present invention comprises at least one compound according to Formula (1) wherein R is linear or branched C16-alkyl and at least one compound according to Formula (1) wherein R is linear or branched C18-alkyl.

In preferred embodiments, the cosmetic composition used in the present invention comprises at least one compound according to Formula (1) wherein R is linear C16-alkyl and at least one compound according to Formula (1) wherein R is linear C18-alkyl.

In preferred embodiments, the cosmetic composition used in the present invention comprises at least one compound according to Formula (1) wherein R is linear or branched C8-alkyl and at least one compound according to Formula (1) wherein R is linear or branched C10-alkyl.

In preferred embodiments, the cosmetic composition used in the present invention comprises at least one compound according to Formula (1) wherein R is linear or branched C10-alkyl and at least one compound according to Formula (1) wherein R is linear or branched C12-alkyl and at least one compound according to Formula (1) wherein R is linear or branched C14-alkyl and at least one compound according to Formula (1) wherein R is linear or branched C16-alkyl.

In some embodiments, the cosmetic composition used in the present invention comprises a mixture of compounds according to Formula (1) having the same n. In other embodiments, the cosmetic composition used in the present invention comprises a mixture of compounds according to Formula (1) wherein n varies from 1 to 20, preferably from 1 to 15, more preferably from 2 to 10, even more preferably from 2 to 8, particularly preferably from 3 to 7. For example, the cosmetic composition used in the present invention comprises a mixture of tetramers (n=3), pentamers (n=4), hexamers (n=5), heptamers (n=6), and octamers (n=7).

Since R cannot be hydrogen, the compound according to Formula (1) is not a carboxylic acid. Acids are not desired as they are prone to instability issues such as self-condensation or hydrolysis over time. The compound according to Formula (1) in contrast provides excellent stability over time, e.g. in storage.

The compound according to Formula (1) is unsaturated. Unsaturated compounds have the advantage that they typically have lower melting points, higher solubility and higher biodegradability.

Compounds according to Formula (1) may be prepared by esterification starting from ricinoleic acid or from commercially available self-condensation products, such as Hostagliss® L2, L4, and L6 (Clariant). The L number of Hostagliss® describes the average degree of oligomerization. L2 refers to a product mixture with an average molecular weight of dimers; L4 refers to a product mixture with an average molecular weight of tetramers; L6 refers to a product mixture with an average molecular weight of hexamers. Preferably, 2 to 6 equivalents of ricinoleic acid are esterified with 0.5 to 2 equivalents of one or more linear or branched C3-C20-alkyl alcohols. The esterification may be acid-catalyzed. Suitable acid catalysts are e.g. hypophosphoric acid, methane sulfonic acid, p-toluene sulfonic acid, phosphoric acid, or sulfuric acid.

In at least one embodiment, the compounds according to Formula (1) have a hydroxy value (OH value) from 1 to 100 mg KOH/g, preferably from 2 to 80 mg KOH/g, more preferably from 3 to 60 mg KOH/g, particularly preferably from 10 to 50 mg KOH/g. The OH value is measured as per ASTM D5558-95 (2011).

Increased hydroxy values may also result from unreacted alcohol in the mixture, so this parameter does not fully characterize the reaction product, if it still contains unreacted alcohol. The acid number can also be used: a lower acid number indicates a lower amount of residual non-esterified estolide, and thus a higher estolide ester content. The acid numbers for the estolide esters described herein are lower than 20 (in preferred embodiments lower than 10). The acid number may be measured using methods such as DIN EN ISO 2114.

In at least one embodiment, the compounds according to Formula (1) have a number average molecular weight (Mn) from 500 to 5000 g/mol, preferably from 1000 to 3000 g/mol, more preferably from 1100 to 2500 g/mol, particularly preferably from 1200 to 2200 g/mol. The molecular weight is measured using gel permeation chromatography (GPC).

Compounds according to Formula (1) may be derived from R-ricinoleic acid, S-ricinoleic acid, or mixtures thereof. In a preferred embodiment, the compounds according to Formula (1) contain more than 70% by weight of the R-ricinoleic acid stereoisomer. In another preferred embodiment, the compounds according to Formula (1) contain more than 70% by weight of the S-ricinoleic acid stereoisomer.

Ricinoleic acid is a naturally occurring fatty acid and therefore a renewable material. In at least one embodiment, the compounds according to Formula (1) are derived from natural and renewable materials, preferably from >90% natural and renewable materials, particularly preferably from 100% natural and renewable materials.

In at least one embodiment, the cosmetic composition comprises from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition.

In preferred embodiments, the cosmetic composition used in the present invention comprises at least one surfactant.

As used herein, "surfactant" means a surface-active agent. In at least one embodiment, the surfactant is an organic amphiphilic compound having at least one hydrophobic portion and at least one hydrophilic portion.

Preferably, the surfactant is selected from the group consisting of anionic surfactants, non-ionic surfactants, cationic surfactants and amphoteric surfactants. More preferably, the surfactant is selected from the group consisting of anionic surfactants, non-ionic surfactants, and amphoteric surfactants.

In at least one embodiment, the surfactant is an anionic surfactant. Examples of suitable anionic surfactants are ammonium lauryl ether sulfate or sodium lauryl ether sulfate (SLES). Examples of other suitable anionic surfactants are polyoxyethylene alkyl ether sulfates such as sodium laureth sulfate, isethionate, taurate, sodium C14-C16 olefin sulfonate, ammonium C12-C15 pareth sulfate, sodium myristyl ether sulfate, or polyoxyethylene alkyl sulfates, such as triethanolamine lauryl sulfate, sodium lauryl sulfate, disodium monooleamidosulfosuccinate, ammonium lauryl sulfosuccinate, sodium dodecylbenzene sulfonate, triethanolamine dodecylbenzene sulfonate, or sodium N-lauroyl sarcosinate.

In at least one embodiment, the surfactant is a non-ionic surfactant. Preferably, the non-ionic surfactant is selected from alkoxylated derivatives of the following: fatty alcohols, alkyl phenols, fatty acids, fatty acid esters or fatty acid amides, in the $C_{16}$ to $C_{40}$ range, and having from about 1 to about 110 alkoxy groups. The alkoxy groups are selected from the group consisting of C2-C6 oxides and their mixtures, with ethylene oxide, propylene oxide, and their mixtures being preferred. The alkyl chain may be linear, branched, saturated, or unsaturated. Alkoxylated alcohols are preferred. Ethoxylated alcohols or propoxylated alcohols are particularly preferred. The alkoxylated alcohols may be used alone or in mixtures.

An example of a commercially available nonionic surfactant is Brij® from Uniqema, Wilmington (USA). Typically, Brij® refers to reaction products of aliphatic alcohols with ethylene oxide. The aliphatic alcohols typically are linear aliphatic alcohols having from 8 to 22 carbon atoms. The ethylene oxide typically is used in a range of from 1 to 54 moles per mole of the aliphatic alcohol. Examples are Brij® 72 (i.e., Steareth-2) and Brij® 76 (i.e., Steareth-10).

Other suitable nonionic surfactants are alkyl glycosides, which are the condensation products of long chain alcohols, e.g. C8-C30 alcohols, with sugar or starch polymers. Examples of alkyl glycosides are decyl polyglucoside or lauryl polyglucoside.

Other suitable nonionic surfactants are glucamide surfactants. Glucamide surfactants are commercially available from Clariant (GlucoTain® or GlucoPure®). In at least one embodiment, the nonionic surfactant is selected from the group consisting of N-methyl-N-acylglucamines, preferably N-methyl-N-acylglucamines of formula (II):

(II)

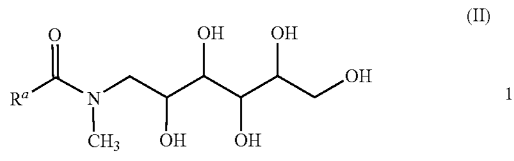

wherein $R^a$ is selected from saturated or unsaturated hydrocarbon chains having 5 to 23 carbon atoms. Preferably, $R^a$ in formula (II) is selected from saturated or unsaturated hydrocarbon chains having 7 to 17 carbon atoms. In preferred embodiments, $R^a$ in formula (II) is selected from saturated hydrocarbon chains having 7 to 17 carbon atoms. In preferred embodiments, $R^a$ in formula (II) is selected from unsaturated hydrocarbon chains having 7 to 17 carbon atoms.

Also preferably, the $R^a$—C═O residue in formula (II) is derived from caprylic acid, capric acid, lauric acid, myristic acid, palmitic acid, stearic acid, oleic acid, linoleic acid, linolenic acid, or mixtures thereof. Also preferably, the $R^a$-C═O residue in formula (II) is derived from coconut oil. Also preferably, the $R^a$-C═O residue in formula (II) is derived from 9-decenoic acid, 9-dodecenoic acid, or mixtures thereof.

Particularly preferred N-methyl-N-acylglucamines of formula (II) are capryloyl/caproyl methyl glucamide, lauroyl/myristoyl methyl glucamide, cocoyl methyl glucamide, oleyl methyl glucamide, or mixtures thereof.

Also particularly preferred N-methyl-N-acylglucamines of formula (II) are N-9-decenoyl-N-methylglucamine, N-9-dodecenoyl-N-methylglucamine, or mixtures thereof.

Other suitable nonionic surfactants are sorbitan esters. Examples of sorbitan esters are sorbitan monopalmitate, Polysorbat 20 or Polysorbat 80. Preferred sorbitan esters are mono-, di-, tri- or tetraesters, or mixtures thereof. More preferred sorbitan esters are mono-, di- or triesters, or mixtures thereof. Particularly preferred sorbitan esters are mono- or diesters, or mixtures thereof. Preferably, the sorbitan esters comprise mixtures of mono-, di-, tri- and tetraesters. More preferably, the sorbitan esters comprise mixtures of mono-, di- and triesters. Particularly preferably, the sorbitan esters comprise mixtures of mono- and diesters. Examples of sorbitan esters are sorbitan caprylate, sorbitan monooleate, sorbitan stearates, sorbitan monoisostearate, or sorbitan sesquioleate.

Preferably, the non-ionic surfactant is selected from glyceryl esters and polyglyceryl esters. Preferred glyceryl fatty acid esters are esters of glycerol and one or more C16-C22 fatty acids. Preferred glyceryl esters are glyceryl mono- or diesters, or mixtures thereof. The fatty acids may be linear or branched, saturated or unsaturated. Examples of glyceryl fatty acid esters are glyceryl oleate, glyceryl monostearate, glyceryl monoisostearate, glyceryl monopalmitate, or glyceryl monobehenate.

Other suitable nonionic surfactants are diethanolam ides (DEA). Examples of diethanolam ides (DEA) are isostearic acid DEA, lauric acid DEA, capric acid DEA, linoleic acid DEA, myristic acid DEA, oleic acid DEA, or stearic acid DEA.

Further nonionic surfactants are selected from the group consisting of fatty acid monoethanolam ides such as coconut fatty acid monoethanolamide, fatty acid monoisopropanolam ides such as oleic acid monoisopropanolamide or lauric acid monoisopropanolamide, alkyl amine oxides such as N-cocodimethylamine oxide, N-lauryl dimethylamine oxide, N-myristyl dimethylamine oxide, or N-stearyl dimethylamine oxide, N-acyl amine oxides such as N-cocoamidopropyl dimethylamine oxide or N-tallowamidopropyl dimethylamine oxide, and N-alkoxyalkyl amine oxides such as bis(2-hydroxyethyl)$C_{12-15}$ alkoxy-propylamine oxide.

In at least one embodiment, the surfactant is an amphoteric surfactant.

Preferably, the amphoteric surfactant is selected from the group consisting of N-($C_{12}$-$C_{18}$)-alkyl-beta-aminopropionates and N-($C_{12}$-$C_{18}$)-alkyl-beta-iminodipropionates as alkali metal salts and mono-, di-, and trialkylammonium salts; N-acylaminoalkyl-N,N-dimethylacetobetaine, preferably N-($C_8$-$C_{18}$)-acylaminopropyl-N,N-dimethylacetobetaine; ($C_{12}$-$C_{18}$)-alkyl-dimethyl-sulfopropylbetaine; amphosurfactants based on imidazoline, preferably the sodium salt of 1-(beta-carboxymethyloxyethyl)-1-(carboxymethyl)-2-laurylimidazolinium; amine oxide, e.g., ($C_{12}$-$C_{18}$)-alkyl-dimethylamine oxide, fatty acid am idoalkyldimethylamine oxide, and mixtures thereof.

Preferred amphoteric surfactants are betaine surfactants. In at least one embodiment, the surfactant is a betaine surfactant.

In preferred embodiments, the betaine surfactant is selected from C8- to C18-alkylbetaines. For example, the betaine surfactant is selected from the group consisting of cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine, laurylbis(2-hydroxypropyl)alphacarboxyethylbetaine, and mixtures thereof.

In preferred embodiments, the betaine surfactant is selected from C8- to C18-sulfobetaines. For example, the betaine surfactant is selected from the group consisting of cocodimethylsulfopropylbetaine, stearyldimethylsulfopropylbetaine, lauryldimethylsulfoethylbetaine, laurylbis(2-hydroxyethyl)sulfopropylbetaine, and mixtures thereof.

In preferred embodiments, the betaine surfactant is selected from carboxyl derivatives of imidazole, C8- to C18-alkyldimethylammonium acetates, C8- to C18 alkyldimethylcarbonylmethylammonium salts, C8- to C18-fatty acid alkylamidobetaines, and mixtures thereof. For example, the C8- to C18-fatty acid alkylamidobetaine is selected from coconut fatty acid am idopropylbetaine, N-coconut fatty acid amidoethyl-N-[2-(carboxymethoxy)ethyl]glycerol (CTFA name: cocoamphocarboxyglycinate), and mixtures thereof.

A particularly preferred amphoteric or betaine surfactant is cocamidopropyl betaine. Another particularly preferred amphoteric or betaine surfactant is sodium cocoamphoacetate.

The above-mentioned surfactants can be used alone or in mixtures.

In at least one embodiment, the cosmetic composition comprises from 0.5 to 80 wt.-%, preferably from 1 to 60 wt.-%, more preferably from 1.5 to 40 wt.-%, particularly preferably from 3 to 25 wt.-% of at least one surfactant, based on the total weight of the cosmetic composition.

In at least one embodiment, the cosmetic composition comprises from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition.

In preferred embodiments, the cosmetic composition used in the present invention comprises at least one rheology modifying agent.

In at least one embodiment, the rheology modifying agent is a compound capable of increasing the viscosity of the composition versus the composition without such compound. In at least one embodiment, the rheology modifying agent is a thickening agent. Thickening agents are herein also referred to as thickeners.

Preferably, the rheology modifying agent is selected from the group consisting of cellulosic thickeners, such as hydroxyethylcellulose, hydroxypropylcellulose, and carboxymethylcellulose, guar gum, such as hydroxypropyl guar, and gums of microbial origin, such as xanthan gum and scleroglucan gum.

Also preferably, the rheology modifying agent is selected from the group consisting of synthetic thickeners, such as crosslinked or non-crosslinked homo- or copolymers of acrylic acid, such as carbomer, and/or of 2-acrylamido-2-methylpropane sulfonic acid or salts thereof.

More preferably, the rheology modifying agent is selected from the group consisting of crosslinked or non-crosslinked homo- or copolymers of 2-acrylamido-2-methylpropane sulfonic acid or salts thereof. Particularly preferably, the rheology modifying agent is selected from the group consisting of crosslinked homo- or copolymers of 2-acrylamido-2-methylpropane sulfonic acid or salts thereof.

In at least one embodiment, the cosmetic composition comprises from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition.

The cosmetic composition used in the present invention comprises an oil phase. Particularly preferably, the cosmetic composition also comprises an aqueous phase.

In preferred embodiments, the cosmetic composition used in the present invention comprises a diluent. Advantageously, the diluent is cosmetically acceptable. Preferred diluents are water, alcohols, or mixtures thereof. More preferred diluents are water, glycerin, ethanol, propanol, isopropanol, ethylene glycol, propylene glycol, or mixtures thereof. A particularly preferred diluent is water. Water is particularly useful for environmental and economic reasons.

The cosmetic composition may comprise further oils. Suitable oils may, for example, be esters of the formula R'COOR", wherein R' and R" are each independently a $C_{4-20}$ linear or branched alkyl, alkenyl or alkoxy-carbonylalkyl or alkylcarbonyl-oxyalkyl. Examples of such esters include isotridecyl isononanoate, PEG-4 diheptanoate (PEG=polyethyleneglycol), isostearyl neopentanoate, tridecyl neopentanoate, cetyl octanoate, cetyl palmitate, cetyl ricinoleate, cetyl stearate, cetyl myristate, isopropyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate. Suitable oils may, for example, also be selected from $C_{10-18}$ triglycerides, castor oil, lanolin oil, triisocetyl citrate, caprylic/capric triglycerides, coconut oil, mineral oil, almond oil, apricot kernel oil, avocado oil, babassu oil, evening primrose oil, camelina sativa seed oil, grape seed oil, macadamia ternifolia seed oil, corn oil, meadowfoam seed oil, mink oil, olive oil, palm kernel oil, safflower oil, sesame oil, soybean oil, sunflower oil, wheat germ oil, and camellia reticulata seed oil.

In preferred embodiments, the cosmetic composition used in the present invention comprises one or more further ingredients. Such further ingredients may, for example, be present in an amount of at least 0.01% by weight, preferably at least 0.05% by weight, more preferably at least 0.1% by weight, even more preferably at least 0.5% by weight, such as 0.01 to 50% by weight, preferably 0.05 to 35% by weight, more preferably 0.1 to 25% by weight, even more preferably 0.5 to 20% by weight of the cosmetic composition. Unless otherwise stated, all percentages are by weight (w/w) of the total composition.

The cosmetic composition used in the present invention may, for example, comprise one or more further ingredients selected from the group consisting of emollients, waxes, surfactants, film formers, superfatting agents, refatting agents, lubricants, foam stabilizers, stabilizers, active biogenic substances, preservatives, preservation boosting ingredients, dyes or pigments, particulate substances, opacifiers, abrasives, absorbents, anticaking agents, bulking agents, pearlizing agents, perfumes or fragrances, vitamins, carriers, propellants, functional acids, active ingredients, skin-brightening agents, self-tanning agents, exfoliants, enzymes, anti-acne agents, deodorants or anti-perspirants, viscosity modifiers, thickening or gelling agents, pH adjusting agents, buffering agents, anti-oxidants, chelants, astringents, sunscreens, sun protection agents, UV filters, conditioning agents, humectants, occlusive agents, anti-foaming agents, flavouring agents, electrolytes, oxidizing agents and reducing agents.

The cosmetic composition may comprise further oils. Suitable oils may, for example, be esters of the formula R'COOR", wherein R' and R" are each independently a $C_{4-20}$ linear or branched alkyl, alkenyl or alkoxy-carbonylalkyl or alkylcarbonyl-oxyalkyl. Examples of such esters include isotridecyl isononanoate, PEG-4 diheptanoate (PEG=polyethyleneglycol), isostearyl neopentanoate, tridecyl neopentanoate, cetyl octanoate, cetyl palm itate, cetyl ricinoleate, cetyl stearate, cetyl myristate, isopropyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate. Suitable oils may, for example, also be selected from $C_{10-18}$ triglycerides, castor oil, lanolin oil, triisocetyl citrate, caprylic/capric triglycerides, coconut oil, mineral oil, almond oil, apricot kernel oil, avocado oil, babassu oil, evening primrose oil, camelina sativa seed oil, grape seed oil, macadamia ternifolia seed oil, corn oil, meadowfoam seed oil, mink oil, olive oil, palm kernel oil, safflower oil, sesame oil, soybean oil, sunflower oil, wheat germ oil, and camellia reticulata seed oil.

In at least one preferred embodiment, the cosmetic composition comprises a preservative. In at least one preferred embodiment, the preservative is selected from the group consisting of benzyl alcohol, piroctone olamine, phenoxyethanol, parabens, pentanediol, benzoic acid, sodium benzoate, sorbic acid, potassium sorbate, and combinations thereof. In at least one preferred embodiment, the preservative is selected from the group consisting of cetyltrimethyl ammonium chloride, cetylpyridinium chloride, benzethonium chloride, diisobutylethoxyethyldimethyl benzylammonium chloride, sodium N-lauryl sarcosinate, sodium-N-palmethyl sarcosinate, lauroyl sarcosine, N-myristoylglycine, potassium-N-laurylsarcosine, trimethylammonium chloride, sodium aluminum chlorohydroxylactate, triethylcitrate, tricetylmethylammonium chloride, 2,4,4'-trichloro-2'-hydroxydiphenylether (Triclosan), phenoxyethanol, 1,5-pentandiol, 1,6-hexandiol, 3,4,4'-trichlorocarbanilide (Triclocarban), diaminoalkylamide, L-lysine hexadecylamide, heavy metal citrate salts, salicylate, piroctose, zinc salts, pyrithione and its heavy metal salts, zinc pyrithione, zinc phenol sulfate, farnesol, ketoconazol, oxiconazol, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, selenium disulfide, piroctone olamine (Octopirox), methylchloroisothiazolinone, methylisothiazolinone, methyldibromoglutaronitrile, silver chloride, diazolidinyl urea, imidazolidinyl urea, dehydroacetic acid, undecylenic acid, chlorphenesin, propionic acid, salicylic acid, chloroxylenol, sodium salts of diethylhexylsulfosuccinate, sodium benzoate, phenoxyethanol, (RS)-1-(4-chlorophenoxy)-1-imidazol-1-yl-3,3-dimethylbutan-2-one (climbazole), benzyl alcohol, phenoxyisopropanol, parabens such as butyl-, ethyl-, methyl- and propylparaben and their salts, 2-bromo-2-nitropropane-1,3-diol, polyaminopropyl biguanide, iodopropynyl butylcarbamate, benzalkonium chloride, benzethonium chloride, pentanediol, 1,2-octanediol, ethylhexylglycerin, sorbic acid, benzoic acid, lactic acid, imidazolidinyl urea, diazolidinyl urea, dimethylol dimethyl hydantoin (DMDMH), chlorhexidine, sodium salts of hydroxymethyl glycinate, and combinations thereof. In at least one preferred embodiment, the composition is substantially free of parabens. In at least one preferred embodiment, the composition comprises from 0.01 wt % to 3 wt %, preferably from 0.05 wt % to 1.5 wt %, more preferably from 0.1 wt % to 1.0 wt % of at least one preservative. In at least one preferred embodiment, the composition comprises a preservation boosting ingredient. In preferred embodiments, the composition comprises a preservative and a preservation boosting ingredient. In at least one preferred embodiment, the preservation boosting ingredient is selected from the group consisting of anisic acid, lactic acid, sorbitan caprylate, ethylhexylglycerin, caprylyl glycol, octanediol, and combinations thereof. In at least one preferred embodiment, the preservation boosting ingredient is capryloyl/caproyl anhydro methyl glucamide. Capryloyl/caproyl anhydro methyl glucamide is commercially available from Clariant (Velsan Flex).

In preferred embodiments, the cosmetic composition comprises at least one active ingredient or at least one sun protection agent and/or UV filter or at least one pigment.

In at least one preferred embodiment, the cosmetic composition comprises an active ingredient. An active ingredient is a substance used to impart a functionality to the skin upon application. Active ingredients are, for example, used as exfoliants, skin brightening agents, self-tanning agents, anti-acne agents, anti-aging agents, anti-wrinkle agents.

Preferably, the active ingredient is selected from the group consisting of skin moisturizing agents, skin softening agents, skin whitening agents, skin lightening agents, exfoliants, anti-aging agents, anti-wrinkle agents, skin barrier repair agents, anti-acne agents, anti-cellulite agents, chemical peeling agents, slimming agents, deodorizing agents, anti-perspirant agents, skin mattifying agents, skin firming agents, skin plumping agents, self-tanning agents, anti-dark circle agents, and skin soothing agents. More preferably, the active ingredient is selected from the group consisting of skin moisturizing agents, skin softening agents, anti-aging agents, anti-wrinkle agents, skin barrier repair agents, and skin soothing agents.

In at least one preferred embodiment, the active ingredient is selected from the group consisting of hydroxy acids, preferably alpha- and beta-hydroxy acids. Examples of preferred hydroxy acids are lactic acid, glycolic acid, salicylic acid and alkylated salicylic acids or citric acid. In at least one preferred embodiment, the active ingredient is selected from the group consisting of tartaric acid, mandelic acid, caffeic acid, pyruvic acid, oligo-oxa mono- and dicarboxylic acids, fumaric acid, retinoic acid, sulfonic acids, benzoic acid, kojic acid, fruit acid, malic acid, gluconic acid, pyruvic acid, galacturonic acid, ribonic acid, hyaluronic acid and derivatives thereof, polyglycol diacids in free or partially neutralized form, vitamin C (ascorbic acid), vitamin C derivatives (e.g. sodium ascorbyl phosphate, magnesium ascorbyl phosphate or magnesium ascorbyl glucoside), dihydroxyacetone, minoxidil, proteolytic enzymes (e.g. fruit enzymes from papaya, pumpkin or pineapple such as papainase and bromelain ananase), caffeine, niacinamide and derivatives thereof, diethyl toluamide (DEET), or skin-whitening actives such as arbutin or glycyrrhetic acid and salts thereof, glutathione, cysteine, resveratrol, 4-butylresorcinol, or plant extracts such as pancratium maritimum extract or mulberry extract. In at least one preferred embodiment, the active ingredient is selected from the group consisting of salicylic acid, kojic acid, hyaluronic acid, ascorbic acid and derivatives thereof, dihydroxyacetone, arbutin, and combinations thereof. In at least one embodiment, the cosmetic composition comprises from 0.05 to 15 wt.-%, preferably from 0.1 to 10 wt.-%, more preferably from 0.3 to 5 wt.-%, particularly preferably from 0.5 to 4 wt.-% of at least one active ingredient, based on the total weight of the cosmetic composition. In at least one embodiment, the cosmetic composition comprises from 0.05 to 15 wt.-%, preferably from 0.1 to 10 wt.-%, more preferably from 0.5 to 5 wt.-%, particularly preferably from 1 to 5 wt.-% of at least one active ingredient, based on the total weight of the cosmetic composition.

In at least one preferred embodiment, the cosmetic composition comprises a sun protection agent and/or UV filter. In preferred embodiments, the sun protection agents and/or UV filters are selected from titanium dioxide, mica-titanium oxide, iron oxides, mica-iron oxide, zinc oxide, silicon oxides, ultramarine blue and chromium oxides. The compositions according to the invention can, for example, comprise titanium dioxide, mica-titanium oxide, iron oxides, mica-iron oxide, zinc oxide, silicon oxides, ultramarine blue or chromium oxides as pigments and as sun protection agents or UV filters. In preferred embodiments, the sun protection agents and/or UV filters are selected from 4-am inobenzoic acid, 3-(4'-trimethylammonium)-benzylidene-bornan-2-one-methylsulfate, camphor benzalkonium methosulfate, 3,3,5-trimethyl-cyclohexylsalicylate, 2-hydroxy-4-methoxybenzophenone, 2-phenylbenzimidazole-5-sulfonic acid and their potassium, sodium and triethanolamine salts, 3,3'-(1,4-phenylenedimethine)-bis(7,7-dimethyl-2-oxobicyclo[2.2.1]-heptane-1-methanesulfonic acid) and salts thereof, 1-(4-tert-butylphenyl)-3-(4-methoxyphenyl)propane-1,3-dione, 3-(4'-sulfo)-benzylidene-bornan-2-one and salts thereof, 2-cyano-3,3-diphenylacrylic acid-(2-ethylhexyl ester), polymers of N-[2(and 4)-(2-oxoborn-3-ylidenemethyl)benzyl]-acrylamide, 4-methoxy-cinnamic acid-2-ethylhexyl ester, ethoxylated ethyl-4-aminobenzoate, 4-methoxy-cinnamic acid isoamyl ester, 2,4,6-tris-[p-(2-ethylhexyloxycarbonyl)anilino]-1,3,5-triazine, 2-(2H-benzotriazol-2-yl)-4-methyl-6-(2-methyl-3-(1,3,3,3-tetramethyl-1-(trimethylsilyloxy)-disiloxanyl)-propyl)phenol, 4,4'-[(6-[4-((1,1-dimethylethyl)-aminocarbonyl)phenylamino]-1,3,5-triazin-2,4-yl)diimino] bis-(benzoic acid-2-ethylhexyl ester), benzophenone-3, benzophenone-4 (acid), 3-(4'-methylbenzylidene)-D,L-camphor, 3-benzylidene-camphor, salicylic acid-2-ethylhexyl ester, 4-dimethylaminobenzoic acid-2-ethylhexyl ester, hydroxy-4-methoxy-benzophenone-5-sulfonic acid (sulfisobenzonum) and the sodium salt, 4-isopropylbenzyl-salicylate, N,N,N-trimethyl-4-(2-oxoborn-3-ylidenemethyl) anilinium methyl sulfate, homosalate, oxybenzone, 2-phenylbenzimidazole-5-sulfonic acid and their sodium, potassium, and triethanolamine salts, octylmethoxycinnamic acid, isopentyl-4-methoxycinnamic acid, isoamyl-p-methoxycinnamic acid, 2,4,6-trianilino-(p-carbo-2'-ethyl-hexyl-1'-oxy)-1,3,5-triazine (octyl triazone) phenol, 2-2(2H-benzotriazol-2-yl)-4-methyl-6-(2-methyl-3-(1,3,3,3-tetramethyl-1-(trimethylsilyl)oxy)-disiloxanyl)propyl (drometrizole trisiloxane) benzoic acid, 4,4-((6-(((1,1-dimethylethyl)amino)carbonyl)phenyl)amino)-1,3,5-triazine-2,4-diyl)diimino)bis,bis(2-ethylhexyl)ester)benzoic acid, 4,4-((6-(((1,1-dimethylethyl)amino)-carbonyl)phenyl)amino)-1,3,5-triazine-2,4-diyl)diimino)bis,bis(2-ethylhexypester), 3-(4'-methylbenzylidene)-D,L-camphor (4-methylbenzylidene camphor), benzylidene-camphor-sulfonic acid, octocrylene, polyacrylamidomethyl-benzylidene-camphor, 2-ethylhexyl salicylate (octyl salicylate), 4-dimethyl-amino-benzoic acid ethyl-2-hexyl ester (octyl dimethyl PABA), PEG-25 PABA, 2-hydroxy-4-m ethoxybenzophenone-5-sulfonic acid (benzophenone-5) and the Na salt, 2,2'-methylene-bis-6-(2H-benzotriazol-2-yl)-4-(tetramethylbutyl)-1,1,3,3-phenol, sodium salt of 2-2'-bis-(1,4-phenylene)1H-benzimidazole-4,6-disulfonic acid, (1,3,5)-triazine-2,4-bis((4-(2-ethylhexyloxy)-2-hydroxy)-phenyl)-6-(4-methoxyphenyl), 2-ethylhexyl-2-cyano-3,3-diphenyl-2-propenoate, glyceryl octanoate di-p-methoxycinnamic acid, p-amino-benzoic acid and esters thereof, 4-tert-butyl-4'-methoxydibenzoylmethane, 4-(2-β-glucopyranoxy) propoxy-2-hydroxybenzophenone, octyl salicylate, methyl-2,5-diisopropylcinnamic acid, cinoxate, dihydroxy-dimethoxybenzophenone, disodium salt of 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl-dimethoxybenzylidene-dioxoimidazolidine propionate, methylene-bis-benzotriazolyl tetramethylbutylphenol, phenyldibenzimidazole tetrasulfonate, bis-ethylhexyloxy-phenol-methoxyphenol-triazine, tetrahydroxybenzophenones, terephthalylidene-dicamphor-sulfonic acid, 2,4,6-tris[4,2-ethylhexyloxycarbonyl)anilino]-1,3,5-triazine, methyl-bis(trimethylsiloxy)silyl-isopentyl trimethoxycinnamic acid, amyl-p-dimethylaminobenzoate, amyl-p-dimethylam inobenzoate, 2-ethylhexyl-p-dimethylaminobenzoate, isopropyl-p-methoxycinnamic acid/diisopropylcinnamic acid ester, 2-ethylhexyl-p-methoxycinnamic acid, 2-hydroxy-4-methoxybenzophenone, 2-hydroxy-4-methoxybenzophenone-5-sulfo acid and the trihydrate, and 2-hydroxy-4-methoxybenzophenone-5-sulfonate sodium salt, phenyl-benzimidazole-sulfonic acid, p-aminobenzoic acid butyl ester, methyl-3-[2,4-bis(methylethyl)phenyl]-2-propenoate, 3-(4-hydroxy)-3-methoxyphenyl)-2-propenoic acid, 5-methyl-2-(1-methylethyl)cyclohexanol-2-aminobenzoate, diethylmalonylbenzylidene oxypropene dimethicone, 2,4,6-tris(biphenyl-4-yl)-1,3,5-triazin and tris(2-hydroxyethyl) ammonium 2-hydroxybenzoate. In at least one preferred embodiment, the sun protection agent and/or UV filter is selected from the group consisting of 2-ethylhexyl 4-methoxycinnamate, methyl methoxycinnamate, 2-ethylhexyl salicylate, 2-ethylhexyl-2-cyano-3,3-diphenyl-2-propenoate, 2-hydroxy-4-methoxybenzophenone-5-sulfonic acid, polyethoxylated p-aminobenzoates, and combinations thereof. In at least one embodiment, the cosmetic composition comprises from 0.01 to 30 wt.-%, preferably from 0.05 to 20 wt.-%, more preferably from 0.1 to 15 wt.-%, particularly preferably from 1 to 10 wt.-% of at least one sun protection agent and/or UV filter, based on the total weight of the cosmetic composition. In at least one embodiment, the cosmetic composition comprises from 0.01 to 40 wt.-%, preferably from 0.05 to 30 wt.-%, more preferably from 0.1 to 20 wt.-%, particularly preferably from 1 to 15 wt.-% of at least one sun protection agent and/or UV filter, based on the total weight of the cosmetic composition. In at least one embodiment, the cosmetic composition comprises at least 2 wt.-%, preferably at least 3 wt.-%, more preferably at least 5 wt.-%, particularly preferably at least 10 wt.-% of at least one sun protection agent and/or UV filter, based on the total weight of the cosmetic composition.

In at least one preferred embodiment, the cosmetic composition comprises a pigment. These may be colored pigments which impart color effects to the product mass or to the skin, or they may be luster effect pigments which impart luster effects to the product mass or to the skin. The color or luster effects on the skin are preferably temporary, i.e. they last until the next skin wash and can be removed by washing the skin with customary body or face cleansers, body or face washes etc. or by using a make-up remover, micellar water or cleansing wipes. In at least one preferred embodiment, the particle size of the pigment is from 1 micron to 200 micron, preferably from 3 micron to 150 micron, more preferably from 10 micron to 100 micron. The pigments are colorants which are virtually insoluble in the application medium, and may be inorganic or organic. Inorganic-organic mixed pigments are also possible. Preference is given to inorganic pigments. The advantage of inorganic pigments is their excellent resistance to light, weather and temperature. The inorganic pigments may be of natural origin. In at least one preferred embodiment, the inorganic pigment is selected from the group consisting of chalk, ochre, umber, green earth, burnt sienna, graphite, and combinations thereof. The pigments may be white pigments, such as, for example, titanium dioxide or zinc oxide, black pigments, such as, for example, iron oxide black, colored pigments, such as, for example, ultramarine or iron oxide red, luster pigments, metal effect pigments, pearlescent pigments, or fluorescent or phosphorescent pigments, where preferably at least one pigment is a colored, nonwhite pigment. In at least one preferred embodiment, the pigment is selected from the group consisting of metal oxides, hydroxides and oxide hydrates, mixed phase pigments, sulfur-containing silicates, metal sulfides, complex metal cyanides, metal sulfates, chromates and molybdates, and the metals themselves (bronze, silver, gold pigments), and combinations thereof. In at least one preferred embodiment, the pigment is selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), and combinations thereof. In at least one preferred embodiment, the pigment is selected from the group consisting of pearlescent and colored pigments which consist of either single crystals like mica, silica, bismuth oxychloride, boron nitride or titanium dioxide or which have a layer-substrate structure based on mica, aluminum, aluminum oxide, titanium dioxide, silicium dioxide, silicates (e.g. calcium aluminum borosilicate, calcium sodium borosilicate, magnesium aluminum silicate or sodium magnesium fluorosilicate) which are coated with a metal oxide (e.g. iron oxide, chromium oxide, tin oxide, titanium dioxide) or a metal oxychloride, such as bismuth oxychloride, or a metal hydroxide, such as aluminum hydroxide, and optionally further color-imparting substances, such as Prussian blue, ultramarine, or carmine and where the color can be determined by varying the layer thickness. The pearlescent effect can be controlled both by means of the particle size and by means of the particle size distribution of the pigment population. Suitable particle size distributions are e.g. in the range 2-50 μm, 5-25 μm, 5-40 μm, 5-60 μm, 5-95 μm, 5-100 μm, 10-60 μm, 10-100 μm, 10-125 μm, 20-100 μm, 20-150 μm, or<15 μm. A wider particle size distribution, e.g. of 20-150 μm, produces glittering effects, whereas a narrower particle size distribution of<15 μm gives a uniform silky appearance. In at least one preferred embodiment, the pigment is selected from the group consisting of titanium dioxide (CI 77891), black iron oxide (CI 77499), yellow iron oxide (CI 77492), red and brown iron oxide (CI 77491), mica, silica, bismuth oxychloride, and combinations thereof. In at least one preferred embodiment, the pigment is selected from the group consisting of organic pigments, such as sepia, gamboge, bone charcoal, Cassel brown, indigo, chlorophyll or other plant pigments. In at least one preferred embodiment, the pigment is selected from the group consisting of synthetic organic pigments, such as azo pigments, anthraquinoids, indigoids, dioxazine, quinacridone, phthalocyanine, isoindolinone, perylene, perinone, metal complex, alkali blue and diketopyrrolopyrrole pigments. In at least one embodiment, the cosmetic composition comprises from 0.1 to 50 wt.-%, preferably from 0.5 to 40 wt.-%, more preferably from 1.0 to 30 wt.-%, particularly preferably from 3.0 to 20 wt.-% of at least one pigment, based on the total weight of the cosmetic composition. In at least one embodiment, the cosmetic composition comprises from 0.01 to 40 wt.-%, preferably from 0.1 to 30 wt.-%, more preferably from 0.5 to 20 wt.-%, particularly preferably from 1 to 10 wt.-% of at least one pigment, based on the total weight of the cosmetic composition. In at least one embodiment, the cosmetic composition comprises at least 3 wt.-%, preferably at least 10 wt.-%, more preferably at least 20 wt.-%, particularly preferably at least 30 wt.-% of at least one pigment, based on the total weight of the cosmetic composition.

Particularly preferably, the cosmetic composition used in the present invention is a skin care composition.

In preferred embodiments, the cosmetic composition used in the present invention is selected from the group consisting of body wash, facial cleanser, cleansing mask, bubble bath, bath oil, cleansing milk, micellar water, make-up remover, cleansing wipes, perfume, soaps, shaving soap, shaving foam, cleansing foam, face mask, intimate wash, micellar water, liquid soap, day cream, anti-aging cream, body milk, body lotion, body mousse, face serum, eye cream, sunscreen lotion, sun cream, face cream, after-shave lotion, pre-shaving cream, depilatory cream, skin-whitening gel, self-tanning cream, anti-acne gel, mascara, foundation, primer, concealer, blush, bronzer, blemish balm (bb) cream, eyeliner, night cream, eye brow gel, highlighter, lip stain, hand sanitizer, nail varnish remover, skin conditioner, split end fluid, deodorant, antiperspirant, baby cream, insect repellent, hand cream, sunscreen gel, foot cream, exfoliator, body scrub, cellulite treatment, bar soap, nail cuticle cream, lip balm, eye shadow, bath additive, body mist, eau de toilette, lubricating gel, moisturizer, serum, toner, aqua sorbet, cream gel, lip stick, lip gloss, hydro-alcoholic gel, body oil, shower milk, illuminator, lip crayon, and sunblock.

In more preferred embodiments, the cosmetic composition used in the present invention is selected from the group consisting of body wash, facial cleanser, bath oil, cleansing milk, shaving foam, face mask, day cream, anti-aging cream, body milk, body lotion, body mousse, face serum, eye cream, sunscreen lotion, sun cream, face cream, after-shave lotion, pre-shaving cream, depilatory cream, blemish balm (bb) cream, night cream, highlighter, lip stain, skin conditioner, deodorant, antiperspirant, baby cream, hand cream, sunscreen gel, foot cream, cellulite treatment, nail cuticle cream, lip balm, bath additive, eau de toilette, lubricating gel, moisturizer, serum, cream gel, lip stick, lip gloss, body oil, shower milk, lip crayon, and sunblock.

In even more preferred embodiments, the cosmetic composition used in the present invention is selected from the group consisting of bath oil, cleansing milk, day cream, anti-aging cream, body milk, body lotion, face serum, eye cream, sunscreen lotion, face cream, pre-shaving cream, night cream, baby cream, hand cream, foot cream, nail cuticle cream, lip balm, moisturizer, lip stick, lip gloss, body oil, and sunblock.

The cosmetic composition used in the present invention can be prepared by methods known in the art. For example, the cosmetic composition used in the present invention can be prepared by mixing its ingredients.

The invention also relates to a method for the cosmetic treatment of skin, wherein the method comprises a) applying a cosmetic composition comprising at least one compound according to Formula (1) as described herein onto skin;
b) optionally removing the cosmetic composition from the skin.

The expression “cosmetic treatment of skin” refers to a non-medical and non-therapeutic treatment.

Preferably, the cosmetic treatment of skin comprises or is selected from skin cleansing, skin moisturizing, skin softening, skin whitening, skin lightening, skin exfoliating, skin anti-aging treatment, skin anti-wrinkle treatment, skin barrier repair treatment, skin anti-acne treatment, skin anti-cellulite treatment, skin depilation, skin shaving, chemical peeling treatment, slimming treatment, skin deodorizing, anti-perspirant treatment, skin mattifying, skin firming, skin plumping, self-tanning treatment, anti-dark circle treatment, UV protection, skin soothing, anti-pollution treatment, nail cuticle treatment, after-sun treatment, and application of color cosmetics.

Also preferably, the cosmetic treatment of skin comprises or is selected from skin cleansing, skin moisturizing, skin softening, skin whitening, skin lightening, skin exfoliating, skin anti-aging treatment, skin anti-wrinkle treatment, skin anti-cellulite treatment, skin depilation, skin shaving, chemical peeling treatment, slimming treatment, skin deodorizing, anti-perspirant treatment, skin mattifying, skin firming, skin plumping, self-tanning treatment, anti-dark circle treatment, skin soothing, anti-pollution treatment, nail cuticle treatment, after-sun treatment, and application of color cosmetics.

Particularly preferably, the cosmetic treatment of skin comprises or is selected from skin moisturizing, skin softening, skin anti-aging treatment, skin anti-wrinkle treatment, skin barrier repair treatment, UV protection, skin soothing and application of color cosmetics.

Also particularly preferably, the cosmetic treatment of skin comprises or is selected from skin moisturizing, skin softening, skin anti-aging treatment, skin anti-wrinkle treatment, skin soothing and application of color cosmetics.

According to step a), a cosmetic composition comprising at least one compound according to Formula (1) as described herein is applied onto skin. The cosmetic composition can be applied onto wet or dry skin.

Step b) is optional. Optionally, the cosmetic composition is removed from the skin. In some embodiments, the cosmetic composition is removed from the skin. In other embodiments, the cosmetic composition is not removed from the skin.

The invention also relates to the use of at least one compound according to Formula (1)

Formula (1)

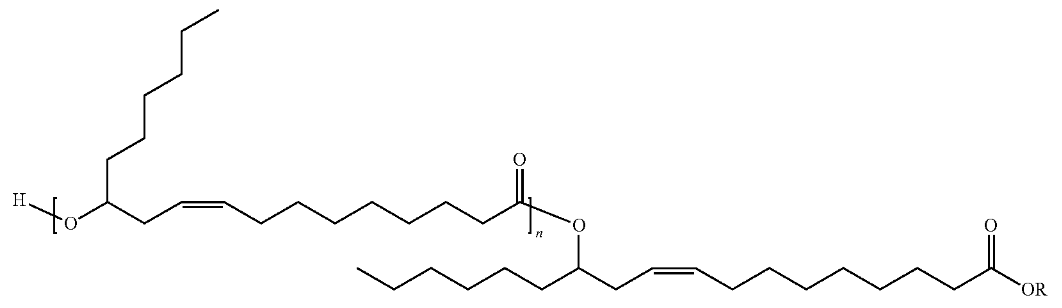

wherein

R is selected from linear or branched C3-C20-alkyl; and n is selected from 1 to 20;

as skin conditioner, dispersing agent, wetting agent, film former, emulsion stabilizer, binding agent, or antifoaming agent in a cosmetic composition.

Preferably, the skin conditioner is an emollient, lubricant, moisturizer, refatting agent, smoothing agent or soothing agent.

The invention also relates to the use of at least one compound according to Formula (1) as defined herein as skin conditioner, emollient, lubricant, moisturizer, refatting agent, smoothing agent, soothing agent, dispersing agent, wetting agent, film former, emulsion stabilizer, binding agent, or antifoaming agent in a cosmetic composition.

Preferably, the compound according to Formula (1) is used as skin conditioner, dispersing agent, wetting agent or film former. More preferably, the compound according to Formula (1) is used as skin conditioner or dispersing agent. Particularly preferably, the compound according to Formula (1) is used as emollient, lubricant, moisturizer, refatting agent, smoothing agent, soothing agent or dispersing agent.

The invention also relates to a cosmetic composition for the cosmetic treatment of skin, wherein the composition comprises at least one compound according to Formula (1)

Formula (1)

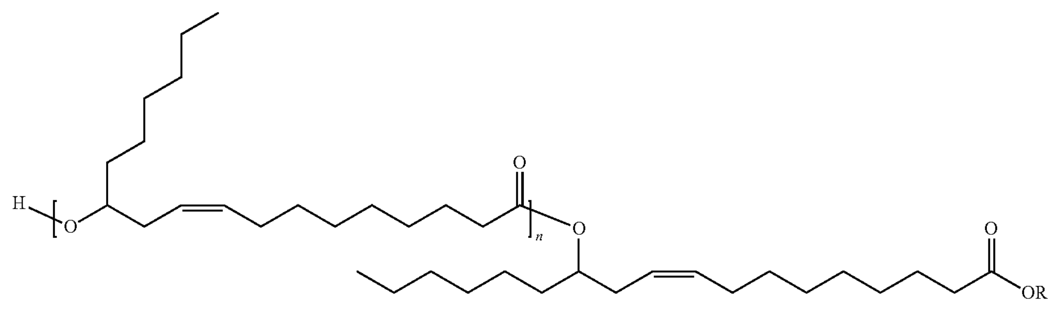

wherein

R is selected from linear or branched C3-C20-alkyl; and n is selected from 1 to 20.

In preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition; and b) from 0.5 to 80 wt.-%, preferably from 1 to 60 wt.-%, more preferably from 1.5 to 40 wt.-%, particularly preferably from 3 to 25 wt.-% of at least one surfactant, based on the total weight of the cosmetic composition.

In preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition; and b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition.

In more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;

b) from 0.5 to 80 wt.-%, preferably from 1 to 60 wt.-%, more preferably from 1.5 to 40 wt.-%, particularly preferably from 3 to 25 wt.-% of at least one surfactant, based on the total weight of the cosmetic composition; and c) from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition.

In more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition; and
c) from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition.

In more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition; and
c) at least one active ingredient or at least one sun protection agent and/or UV filter or at least one pigment.

In even more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) from 0.05 to 15 wt.-%, preferably from 0.1 to 10 wt.-%, more preferably from 0.5 to 5 wt.-%, particularly preferably from 1 to 5 wt.-% of at least one active ingredient, based on the total weight of the cosmetic composition.

In even more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) from 0.01 to 40 wt.-%, preferably from 0.05 to 30 wt.-%, more preferably from 0.1 to 20 wt.-%, particularly preferably from 1 to 15 wt.-% of at least one sun protection agent and/or UV filter, based on the total weight of the cosmetic composition.

In even more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) from 0.01 to 40 wt.-%, preferably from 0.1 to 30 wt.-%, more preferably from 0.5 to 20 wt.-%, particularly preferably from 1 to 10 wt.-% of at least one pigment, based on the total weight of the cosmetic composition.

In more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition; and
d) at least one active ingredient or at least one sun protection agent and/or UV filter or at least one pigment.

In even more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) optionally from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition; and
d) from 0.05 to 15 wt.-%, preferably from 0.1 to 10 wt.-%, more preferably from 0.5 to 5 wt.-%, particularly preferably from 1 to 5 wt.-% of at least one active ingredient, based on the total weight of the cosmetic composition.

In some embodiments, the at least one rheology modifying agent is present.

In even more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) optionally from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition; and
d) from 0.01 to 40 wt.-%, preferably from 0.05 to 30 wt.-%, more preferably from 0.1 to 20 wt.-%, particularly preferably from 1 to 15 wt.-% of at least one sun protection agent and/or UV filter, based on the total weight of the cosmetic composition.

In some embodiments, the at least one rheology modifying agent is present.

In even more preferred embodiments, the cosmetic composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) optionally from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition; and
d) from 0.01 to 40 wt.-%, preferably from 0.1 to 30 wt.-%, more preferably from 0.5 to 20 wt.-%, particularly preferably from 1 to 10 wt.-% of at least one pigment, based on the total weight of the cosmetic composition.

In some embodiments, the at least one rheology modifying agent is present.

Particularly preferably, the cosmetic composition comprises water. The cosmetic composition may, for example, comprise at least 10 wt.-%, preferably at least 20 wt.-%, more preferably at least 30 wt.-%, even more preferably at least 40 wt.-%, particularly preferably at least 50 wt.-%, or at least 60 wt.-%, or at least 70 wt.-%, or at least 80 wt.-% water, based on the total weight of the cosmetic composition.

The embodiments described herein for the cosmetic composition used in the present invention also apply to the cosmetic composition of the present invention.

Likewise, the embodiments described herein for the cosmetic composition of the present invention also apply to the cosmetic composition used in the present invention.

The invention also relates to a composition comprising at least one compound according to Formula (1) as described herein for use in skin barrier repair treatment, skin anti-acne treatment, or UV protection of skin. In a preferred embodiment, the composition comprising at least one compound according to Formula (1) as described herein is for use in skin barrier repair treatment or UV protection of skin. In a particularly preferred embodiment, the composition comprising at least one compound according to Formula (1) as described herein is for use in UV protection of skin. Preferred compounds according to Formula (1) are described further above.

In preferred embodiments, the composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) from 0.01 to 40 wt.-%, preferably from 0.05 to 30 wt.-%, more preferably from 0.1 to 20 wt.-%, particularly preferably from 1 to 15 wt.-% of at least one sun protection agent and/or UV filter, based on the total weight of the cosmetic composition.

In preferred embodiments, the composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) optionally from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition; and
d) from 0.01 to 40 wt.-%, preferably from 0.05 to 30 wt.-%, more preferably from 0.1 to 20 wt.-%, particularly preferably from 1 to 15 wt.-% of at least one sun protection agent and/or UV filter, based on the total weight of the cosmetic composition.

In some embodiments, the at least one rheology modifying agent is present.

In preferred embodiments, the composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;
b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;
c) from 0.05 to 15 wt.-%, preferably from 0.1 to 10 wt.-%, more preferably from 0.5 to 5 wt.-%, particularly preferably from 1 to 5 wt.-% of at least one active ingredient, based on the total weight of the cosmetic composition.

In preferred embodiments, the composition comprises a) from 0.1 to 20 wt.-%, preferably from 0.5 to 10 wt.-%, more preferably from 1 to 5 wt.-%, particularly preferably from 1 to 3 wt.-% of at least one compound according to Formula (1), based on the total weight of the cosmetic composition;

b) from 0.01 to 20 wt.-%, preferably from 0.05 to 10 wt.-%, more preferably from 0.1 to 5 wt.-%, particularly preferably from 0.5 to 3 wt.-% of at least one surfactant, based on the total weight of the cosmetic composition;

c) optionally from 0.01 to 10 wt.-%, preferably from 0.05 to 5 wt.-%, more preferably from 0.1 to 3 wt.-%, particularly preferably from 0.2 to 2 wt.-% of at least one rheology modifying agent, based on the total weight of the cosmetic composition; and d) from 0.05 to 15 wt.-%, preferably from 0.1 to 10 wt.-%, more preferably from 0.5 to 5 wt.-%, particularly preferably from 1 to 5 wt.-% of at least one active ingredient, based on the total weight of the cosmetic composition.

In some embodiments, the at least one rheology modifying agent is present.

The invention is further illustrated by the following examples.

EXAMPLES

Materials and Methods

The molecular weight is measured using gel permeation chromatography (GPC) using a modified styrene divinylbenzene copolymer as column material. The following columns are used: 1×guard column, 10 μm, 50 mm×8 mm ID and 2×GPC columns 100 Å, 5 μm, 300 mm×8 mm ID (PSS SDV).

Calibration is done with polystyrene in the range from 682 to 28000 g/mol, and detection is done with an evaporative light scattering detector (ELSD).

Tetrahydrofuran is used as eluent, injection volume is 2 μL, and experiments are performed at 40° C. at the flow rate of 1.0 mL/min.

Hostagliss® L4 (Clariant) is a self-condensation product mixture with an average molecular weight of tetramers (approximately 1300 g/mol). The viscosity (20° C.) is approximately 1100 mPa s (DIN ISO 53015, 2001-02).

For the calculation of the mass of Hostagliss® L4 and ricinoleic acid to be used in reactions to obtain compounds of the Examples 3, 5 and 6, the active levels of the acid (in technical grade materials) are calculated from the acid numbers which are determined experimentally.

Example 1

Preparation of Estolide Ester from Hostagliss® L4 (Clariant) and 2-Ethylhexanol

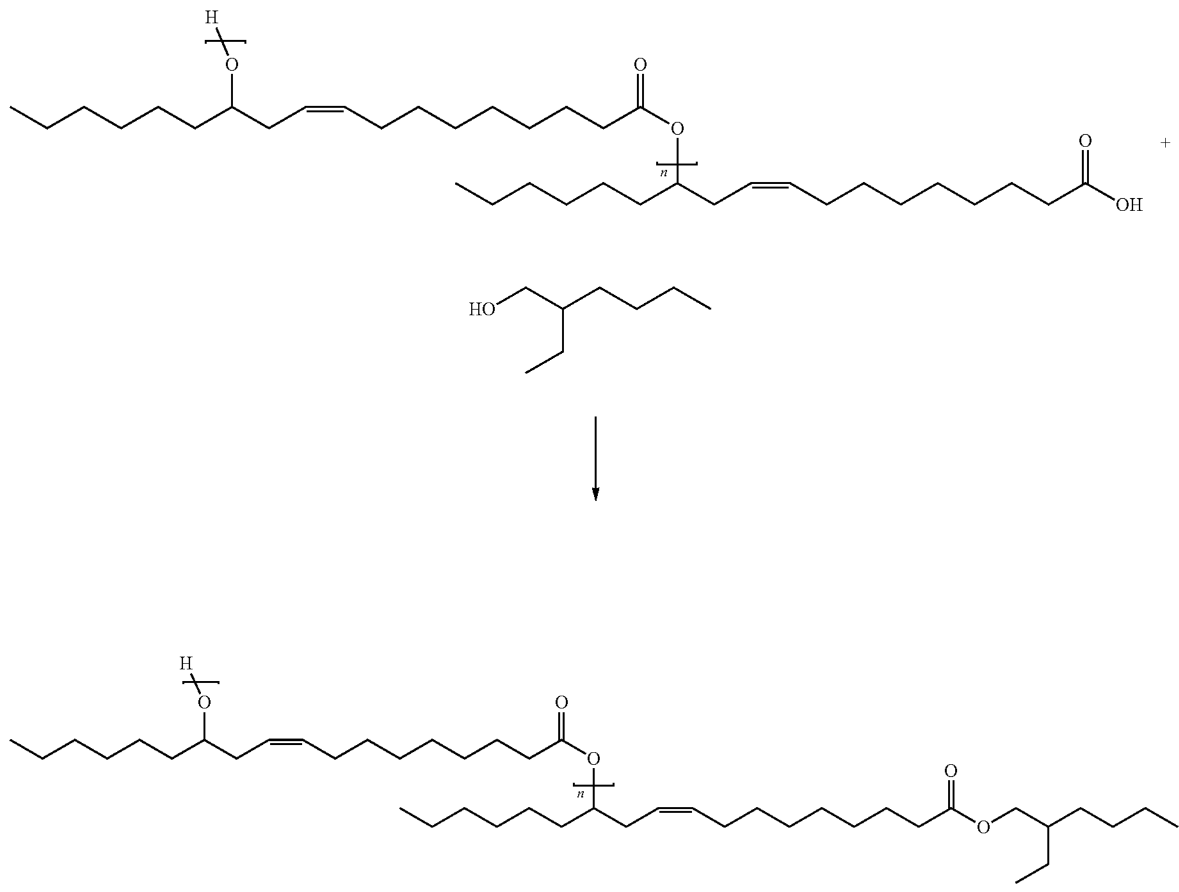

Hostagliss® L4 (300.1 g) is charged into a 1 L, 4-necked flask with a stirrer, a reflux condenser and a thermometer, and set under nitrogen atmosphere. Hypophosphoric acid (1.7 g) is added via a syringe and 2-ethylhexanol (34.3 g) is subsequently added drop-wise over a period of 10 min. The reaction mixture is heated to 160° C. and refluxed for one hour. Subsequently the reflux condenser is replaced with a distillation bridge and the volatiles are distilled off over 19 h at 160° C. The product (276.9 g) is filled into a flask for storage and analyzed.

Example 2

Preparation of Estolide Ester from Ricinoleic Acid (4 Eq.) and 2-Ethylhexanol

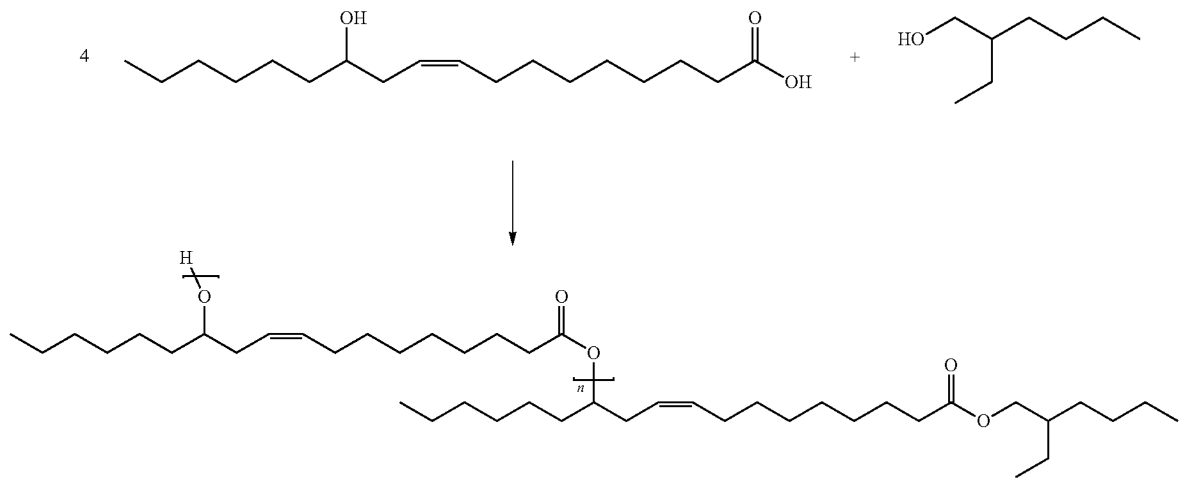

A 500 mL, 4-necked round bottom flask with stirrer, thermometer and a distillation bridge is set under nitrogen atmosphere and charged with ricinoleic acid (298.5 g) and 2-ethylhexanol (32.6 g). The reaction mixture is heated to 170° C. and the volatiles are distilled off for 4.5 h. Subsequently, methane sulfonic acid (0.56 g) is added and the reaction mixture is heated to 166-170° C. for 9 h and the volatiles are distilled off. The product (258.4 g) is filled into a flask for storage and analyzed.

Example 3

Preparation of Estolide Ester from Ricinoleic Acid (2 Eq.) and 2-Ethylhexanol

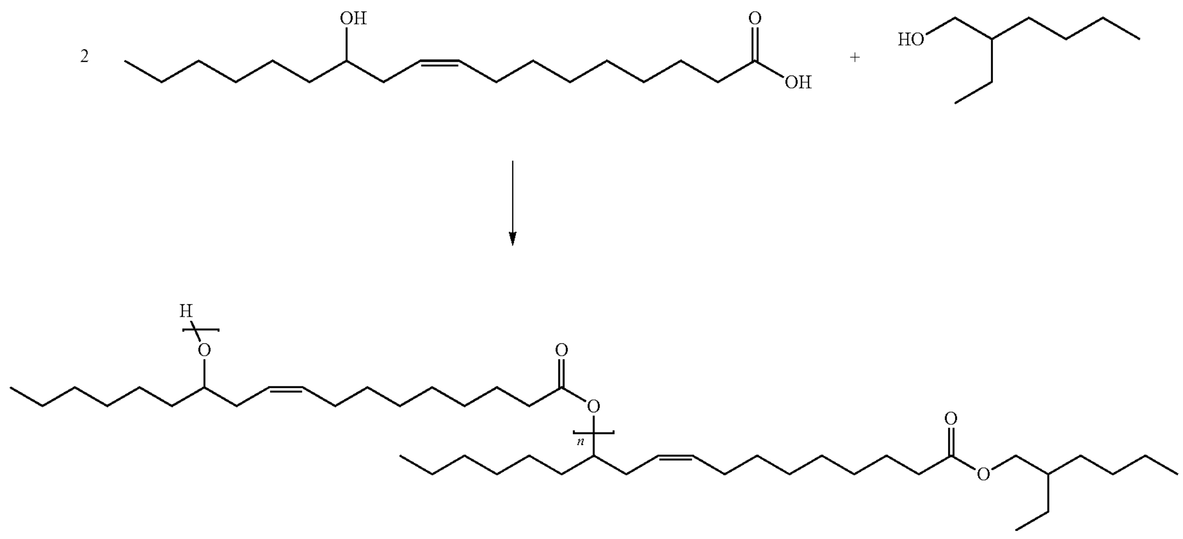

A 500 mL, 4-necked round bottom flask with stirrer, thermometer and a distillation bridge is set under nitrogen atmosphere and charged with ricinoleic acid (320.1 g) and 2-ethylhexanol (63.2 g). The reaction mixture is heated to 170° C. and the volatiles are distilled off for 3 h. Subsequently, p-toluene sulfonic acid (0.95 g) is added and the reaction mixture is heated to 166-170° C. for 9 h and the volatiles are distilled off. The product (330.0 g) is filled into a flask for storage and analyzed.

Example 4

Preparation of Estolide Ester from Hostagliss® L4 and Decanol

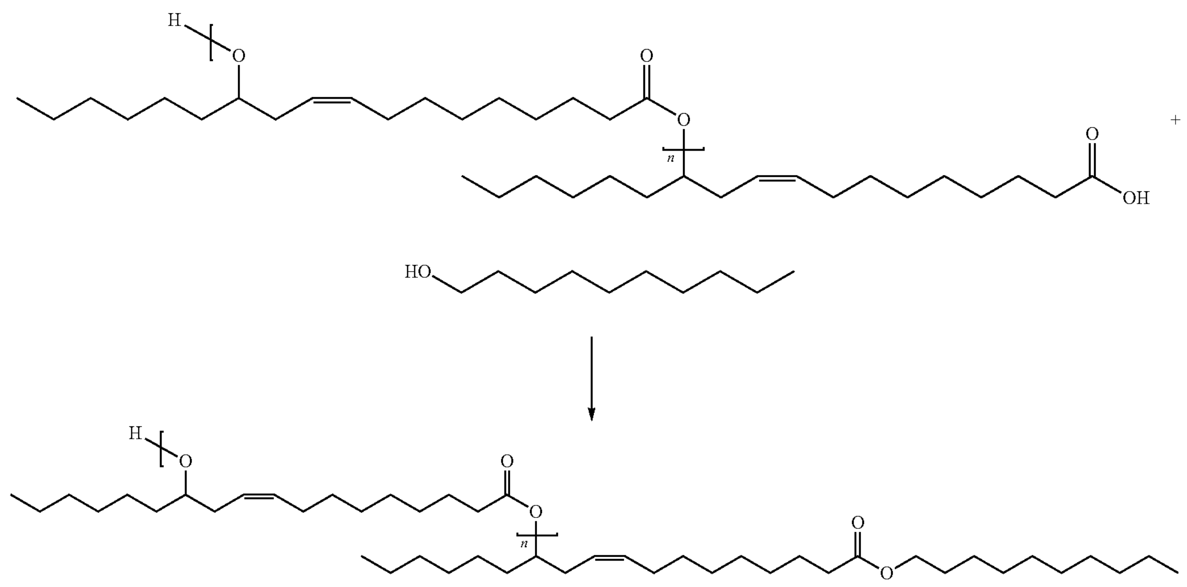

Hostagliss® L4 (300.0 g) is charged into a 500 mL, 4-necked flask with a stirrer, a reflux condenser and a thermometer and set under nitrogen atmosphere.

Hypophosphoric acid (1.7 g) is added via a syringe and 1-decanol (41.6 g) is subsequently added drop-wise over a period of 10 min. The reaction mixture is heated to 155-165° C. and refluxed for one hour. Subsequently, the reflux condenser is replaced with a distillation bridge and the volatiles are distilled off for 16 hat 165-178° C. The product (285.1 g) is filled into a flask for storage and analyzed.

Example 5

Preparation of Estolide Ester from Ricinoleic Acid (2 Eq.) and Decanol

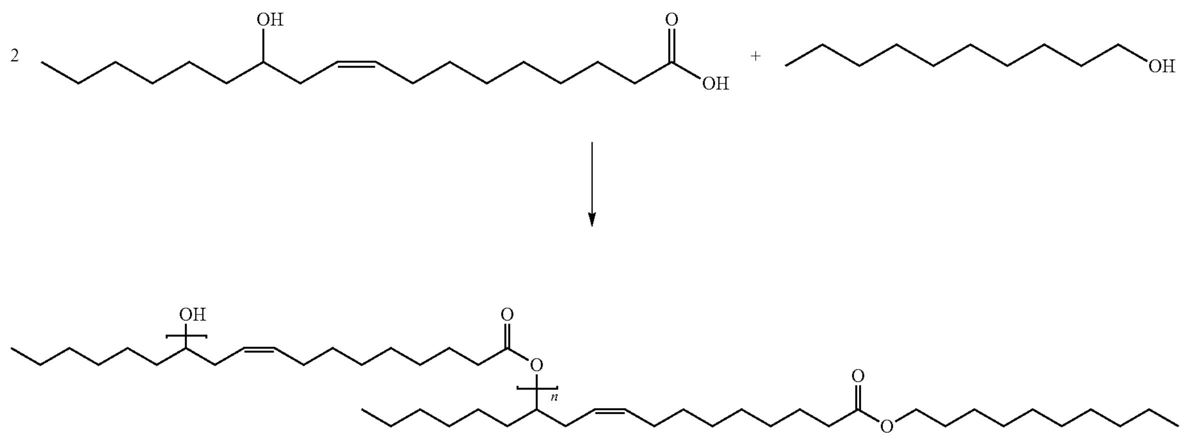

A 500 mL, 4-necked round bottom flask with stirrer, thermometer and a distillation bridge is set under nitrogen atmosphere and charged with ricinoleic acid (320.1 g) and 1-decanol (79.2 g). The reaction mixture is heated to 170° C. and the volatiles are distilled off for 5 h. Subsequently, p-toluene sulfonic acid (0.95 g) is added and the reaction mixture is heated to 149-168° C. for 6 h and the volatiles are distilled off. The product (359.5 g) is filled into a flask for storage and analyzed.

Example 6

Preparation of Estolide Ester from Ricinoleic Acid (4 Eq.) and Decanol

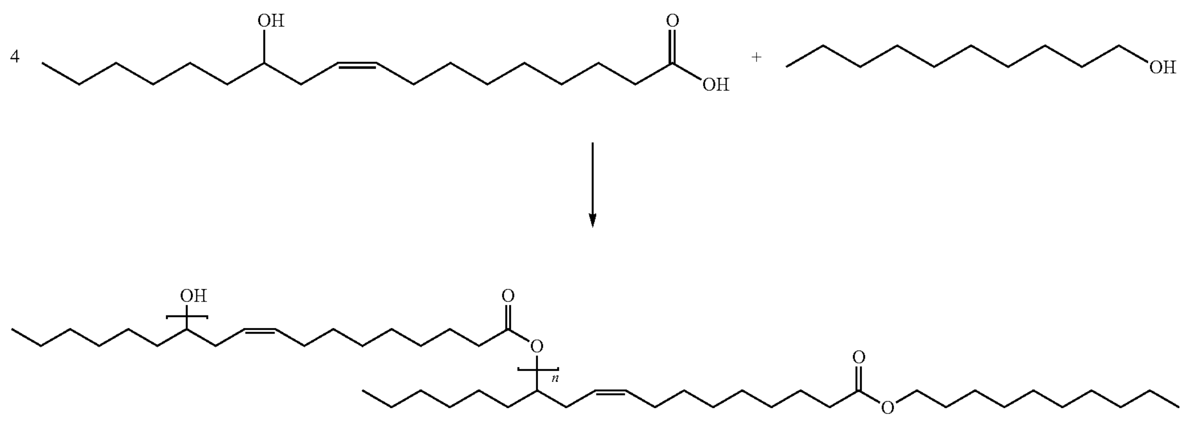

A 500 mL, 4-necked round bottom flask with stirrer, thermometer and a distillation bridge is set under nitrogen atmosphere and charged with ricinoleic acid (320.1 g) and 1-decanol (39.6 g). The reaction mixture is heated to 170° C. and the volatiles are distilled off for 4 h. Subsequently, p-toluene sulfonic acid (0.95 g) is added and the reaction mixture is heated to 156-174° C. for 33 h and the volatiles are distilled off. The product (289.0 g) is filled into a flask for storage and analyzed.

Example 6a

Preparation of Estolide Ester from Ricinoleic Acid (4 Eq.) and Lauryl Alcohol (Dodecanol). Lauryl Alcohol Can Be Purchased from Kao (Kalcol 2098)

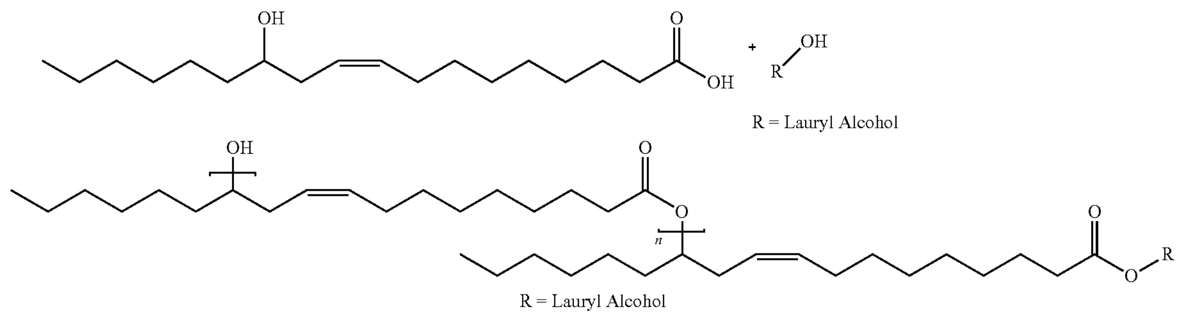

A 500 mL, 4-necked round bottom flask with stirrer, thermometer and a distillation bridge is set under nitrogen atmosphere and charged with ricinoleic acid (320.1 g), p-toluene sulfonic acid (0.95 g) and Lauryl alcohol (45.8 g). The reaction mixture is heated to 170° C. and the volatiles are distilled off for 13 h. The product (312.3 g) is filled into a flask for storage and analyzed.

Example 6b

Preparation of Estolide Ester from Ricinoleic Acid (4 Eq.) and Lauryl-Myristyl Alcohol. Lauryl-Myristyl Alcohol Can Be Purchased from Wilmar (Wilfarol 1214)

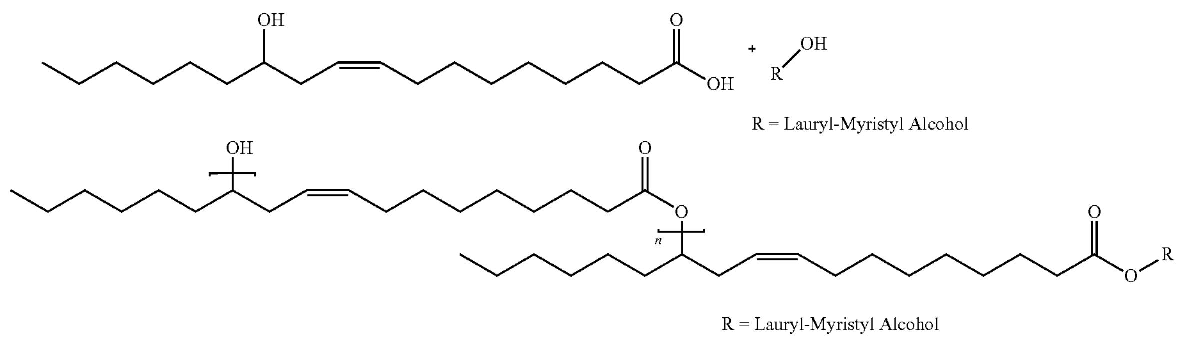

R = Lauryl-Myristyl Alcohol

R = Lauryl-Myristyl Alcohol

A 500 mL, 4-necked round bottom flask with stirrer, thermometer and a distillation bridge is set under nitrogen atmosphere and charged with ricinoleic acid (320.1 g), p-toluene sulfonic acid (0.95 g) and Lauryl-Myristyl alcohol (48.5 g). The reaction mixture is heated to 170° C. and the volatiles are distilled off for 13 h. The product (312.3 g) is filled into a flask for storage and analyzed.

TABLE 1

Summary and analytical data of Examples 1 to 6, 6a and 6b

| Example number | Starting material (estolide or fatty acid) | Starting material (alcohol) | OH value (mg KOH/g) | $M_n$ (g/mol) | Acid value (mg KOH/g) |
|---|---|---|---|---|---|
| 1 | Hostagliss ® L4 | 2-ethylhexanol | 17 | 2029 | 4.8 |
| 2 | Ricinoleic acid (4 eq.) | 2-ethylhexanol | 19 | 2143 | 4.4 |
| 3 | Ricinoleic acid (2 eq.) | 2-ethylhexanol | 46 | 1261 | 4.0 |
| 4 | Hostagliss ® L4 | Decanol | 16 | 1973 | 4.3 |
| 5 | Ricinoleic acid (2 eq.) | Decanol | 44 | 1886 | 2.2 |
| 6 | Ricinoleic acid (4 eq.) | Decanol | 11 | 1884 | 6.0 |
| 6a | Ricinoleic acid (4 eq.) | Lauryl alcohol | 15 | 1928 | 3.7 |
| 6b | Ricinoleic acid (4 eq.) | Lauryl-Myristyl-Alcohol | 12 | 1927 | 1.4 |

Examples 7 to 11

The "Lauryl/Myristyl Polyricinoleate" referred to in Examples 7 to 11 is a mixture of compounds according to Formula (1), wherein the mixture has a number average molecular weight Mn of approx. 2600 g/mol. The level of active of said "Lauryl/Myristyl Polyricinoleate" is>95%.

Example 7: Technical Parameters

The following technical parameters were determined for Lauryl/Myristyl Polyricinoleate:

Spreadability [$mm^2$/10 min]: 180

Refractive index, determined according to DIN ISO 6320: 2017 [20° C.]: 1.4737

Surface tension [mN/m], determined according to EN 14370 [25° C.]: 34

The spreadability was determined as follows:

Vitro-Skin® hydration protocol: Vitro-Skin® pieces must be stored for a period of 16 to 24 hours on the shelf of a standardized hydration chamber with a 350 g mixture of glycerol (15%) and water (85%) at the bottom.

The spreading value will be defined as the surface area covered by 10 μl of oil mixture after 10 minutes.

The liquid will be dropped into the center of a hydrated Vitro-Skin® piece measuring 65×65 mm using a manual micropipette from Fa. Mettler-Toledo LLC, Ohio, USA.

The Vitro-Skin® sample will be kept in the hydration chamber for 10 min according to the spreading phase.

After 10 minutes, the outline of the spreading surface will be determined visually, and the spread will be determined using a ruler.

The spreading area will be calculated using the circular area formula: $A=\pi r^2$ [A: area; π: circle number (3.14159 . . . ); r: radius of the circle calculated].

Measurements will be performed in triplicate at room temperature.

The spreading values are given in $mm^2$ (the higher the value, the higher the spread).

Example 8: Compatibility with Waxes and Oils

Mixtures of Lauryl/Myristyl Polyricinoleate and 5% wax were tested. Smooth oleogels were formed with natural waxes like Candelilla wax, Carnauba wax or Beeswax. Lauryl/Myristyl Polyricinoleate shows excellent compatibility with natural, synthetic or animal derived waxes:

| Wax | Appearance hot | Appearance cold | Compatibility | Oleogel |
|---|---|---|---|---|
| Beeswax | homogeneous transparent | homogeneous semisolid oleogel | *** | ** |
| Carnauba Wax | homogeneous transparent | homogeneous soft semisolid oleogel | *** | * |
| Ozokerite | homogeneous transparent | homogeneous semisolid oleogel | *** | ** |
| Candelilla Wax | homogeneous transparent | homogeneous smooth semisolid oleogel | *** | *** |
| Cera Micro-cristallina | homogeneous transparent | homogeneous opaque | *** | — |

Compatibility:
* good,
** very good,
*** excellent

Lauryl/Myristyl Polyricinoleate was mixed in a 1:1 ratio with Mineral Oil, Caprylic/Capric Triglyceride or Castor Oil. Lauryl/Myristyl Polyricinoleate shows excellent compatibility with various oils:

| Oil | Appearance | Compatibility |
|---|---|---|
| Mineral Oil | clear homogeneous | *** |
| Caprylic/Capric Triglyceride | clear homogeneous | *** |
| Castor Oil | clear homogeneous | *** |

Compatibility:
* good,
** very good,
*** excellent

Example 9: Compatibility with UV Filters 5 or 10% of a UV filter was mixed with Lauryl/Myristyl Polyricinoleate at elevated temperatures until the mixture was homogeneous. All UV filters were tested up to the maximum % allowed by global regulations: Eclipsogen EHT up to 5%, Eclipsogen AVB, Sorb S and BP3 up to 10%.

| UV Filter | Appearance hot | Appearance cold after 24 h | Compatibility |
|---|---|---|---|
| Eclipsogen EHT Ethylhexyl Triazone | homogeneous transparent | homogeneous transparent | *** |
| Eclipsogen AVB Butyl Methoxy-dibenzoylmethane (Avobenzone) | homogeneous transparent | homogeneous transparent | *** |
| Eclipsogen Sorb S Bis-Ethylhexyloxyphenol Methoxyphenyl Triazine | homogeneous transparent | homogeneous transparent | *** |
| Eclipsogen BP3 Benzophenone-3 (Oxybenzone) | homogeneous transparent | homogeneous transparent | *** |

Compatibility:
* good,
** very good,
*** excellent

Lauryl/Myristyl Polyricinoleate shows excellent solubilisation of crystalline UV filters. These results show that Lauryl/Myristyl Polyricinoleate is very useful for sun care applications.

Example 10: Pigment Wetting

The viscosity of a pigment dispersion in oil is negatively correlated to the dispersion efficacy of the carrier liquid emollient. Therefore, decreased viscosities confirm the homogeneity of the dispersion. To calculate the viscosity difference rate between the pure emollient without added pigment and the pigment dispersion, the following formula will be used:

Viscosity difference rate=(viscosity value after pigment dispersion−viscosity value before pigment dispersion)/(viscosity value before pigment dispersion)

The lower the viscosity difference rate the better the pigment wetting.

Mixtures of 65% emollient with 35% pigment (red iron oxide) were homogenized and analyzed*.

| Emollient | Viscosity difference rate |
|---|---|
| Lauryl/Myristyl Polyricinoleate | 4 |
| Castor Oil** | 5 |
| Pentaerythrityl Tetraisostearate** | 21 |
| C12-C15 Alkylbenzoate** | 60 |
| Caprylic/Capric Triglyceride** | 67 |

* Rheometer: HAAKE Mars III with Plate P35 Ti L - 14048 (plate-and-plate method, gap 0.200 mm), average of 3 measurements: 30.0 s @ 20.0° C. as set temperature and sheer rate of 10.0 1/s
**Comparative example Lauryl/Myristyl Polyricinoleate shows excellent wetting of pigments. These results show that Lauryl/Myristyl Polyricinoleate is very useful for color cosmetic applications.

Example 11: Pigment Dispersion

Mixtures of 65% emollient with 35% pigment (yellow iron oxide) were homogenized and analyzed*.

| Emollient | Average particle size/μm |
|---|---|
| Lauryl/Myristyl Polyricinoleate | 14.3 |
| Castor Oil** | 17.7 |
| Pentaerythrityl Tetraisostearate** | 31 |

-continued

| Emollient | Average particle size/μm |
|---|---|
| Caprylic/Capric Triglyceride** | 80.3 |
| C12-C15 Alkylbenzoate** | 85 |

* 2 min Ultra-Turrax @ 13.000 rpm; measurement (next day): average of 3 measurements with Grindometer (0-100 μm, Thierry GmbH)
**Comparative example Lauryl/Myristyl Polyricinoleate shows excellent dispersion of pigments with low average particle size. The dispersion with Lauryl/Myristyl Polyricinoleate also shows excellent color intensity. These results show that Lauryl/Myristyl Polyricinoleate is very useful for color cosmetic applications.

Examples of Skin Care Compositions

Skin care compositions according to the invention can be prepared by mixing their components.

Example 1: Sun Cream SPF 50+, PA++++

| Ingredient | wt % |
|---|---|
| Water | ad 100 |
| Glycerin (85%) | 3.00 |
| Eclipsogen ® PBSA | 2.00 |
| Phenylbenzimidazole Sulfonic Acid | |
| Sodium Hydroxide | q.s. to pH 7 |
| Hostaphat ® KL 340 D (Clariant) | 0.75 |
| Trilaureth-4 Phosphate | |
| Cetearyl Alcohol | 2.25 |
| Lauryl/Myristyl Polyricinoleate & Glycerin | 2.00 |
| Plantasens ® Olive LD (Clariant) | 4.00 |
| Hydrogenated Ethylhexyl Olivate, Hydrogenated Olive Oil Unsaponifiables | |
| Eclipsogen ® Sorb S (Clariant) | 5.00 |
| Bis-Ethylhexyloxylphenol Methoxyphenyl Triazine | |
| Eclipsogen ® OC (Clariant) | 6.00 |
| Octocrylene | |
| Eclipsogen ® EHT (Clariant) | 3.00 |
| Ethylhexyl Triazone | |
| Eclipsogen ® Sorb M (Clariant) | 10.00 |
| Methylene Bis-Benzotriazolyl Tetramethylbutylphenol (and) Aqua (and) Decyl Glucoside (and) Propylene Glycol (and) Xanthan Gum | |
| Aristoflex ® Silk (Clariant) | 1.50 |
| Sodium Polyacryloyldimethyl Taurate | |
| Nipaguard ® PO 5 (Clariant) | 1.00 |
| Phenoxyethanol, Piroctone Olamine | |
| Fragrance | 0.30 |

Viscosity: 25,000 mPas; pH: 7.0

Example 2: Caring Baby Lotion

| Ingredient | wt % |
|---|---|
| SilCare ® Silicone 41M15 (Clariant) | 4.00 |
| Caprylyl Methicone | |
| Cyclopentasiloxane/Cyclohexasiloxane | 10.00 |
| Zinc Oxide (and) Triethoxycaprylylsilane | 10.00 |
| Lauryl/Myristyl Polyricinoleate & Glycerin | 2.00 |
| Ethylhexyl Stearate | 2.00 |
| Titanium Dioxide | 6.00 |
| Cetyl PEG/PPG-10/1 Dimethicone | 2.00 |
| SilCare ® Silicone 41M65 (Clariant) | 1.00 |
| Stearyl Dimethicone | |

-continued

| Ingredient | wt % |
|---|---|
| Plantasens ® Emulsifier DGI (Clariant) | 2.00 |
| Polyglyceryl-2 Sesquiisostearate | |
| Water | q.s. |
| Glycerin (85%) | 5.00 |
| Disodium EDTA | 0.20 |
| Citric Acid | 0.10 |
| Sodium Chloride | 1.00 |
| Tocopheryl Acetate | 1.00 |
| Nipaguard ® SCP (Clariant) | 1.40 |
| Phenoxyethanol, Sorbitan Caprylate | |

Viscosity: 9,750 mPas; pH: 6.5

Example 3: Moisturising Body Butter

| Ingredient | wt % |
|---|---|
| Plantasens ® Refined Shea Butter (Clariant) | 3.00 |
| *Butyrospermum Parkii* (Shea Butter) | |
| Cetearyl Alcohol | 1.00 |
| Caprylic/Capric Triglyceride | 4.00 |
| Lauryl/Myristyl Polyricinoleate & Glycerin | 5.00 |
| Myristyl Myristate | 1.00 |
| Plantasens ® Emulsifier HE 20 (Clariant) | 5.00 |
| Cetearyl Glucoside, Sorbitan Olivate | |
| Aristoflex ® HMB (Clariant) | 1.00 |
| Ammonium Acryloyl Dimethyl Taurate/Beheneth-25 Methacrylate Crosspolymer | |
| Water | ad 100 |
| Genapol ® G 260 (Clariant) | 5.00 |
| Glycereth-26 | |
| Citric acid | q.s. |
| Nipaguard ™ POB (Clariant) | 1.00 |
| Phenoxyethanol (and) Benzoic Acid (and) Piroctone Olamine | |

Viscosity: 68,000 mPas; pH: 6.0

Example 4: Daily BB Serum with SPF 10 and UVA

| Ingredient | wt % |
|---|---|
| Water | ad 100 |
| Glycerin (85%) | 2.00 |
| Aristoflex ® AVC (Clariant) | 1.20 |
| Ammonium AcryloyldimethylTaurate/VP Copolymer | |
| Chroma-Lite ® (BASF) | 0.75 |
| Mica (and) Bismuth Oxychloride (and) Iron Oxide | |
| Titanium Dioxide | 1.50 |
| Butylene Glycol | 4.00 |
| Hostaphat ® KL 340 D (Clariant) | 3.00 |
| Trilaureth-4 Phosphate | |
| Plantasens ® Emulsifier CP 5 (Clariant) | 1.00 |
| Glyceryl Oleate, Polyglyceryl-3 Polyricinoleate, *Olea Europaea* (Olive) Oil Unsaponifiables | |
| Octocrylene | 5.00 |
| Butyl Methoxydibenzoylmethane | 0.50 |
| Plantasens ® Olive LD (Clariant) | 2.00 |
| Hydrogenated Ethylhexyl Olivate, Hydrogenated Olive Oil Unsaponifiables | |
| Lauryl/Myristyl Polyricinoleate & Glycerin | 4.00 |
| C12-15 Alkyl Benzoate | 7.00 |
| Dicaprylyl Ether | 2.00 |
| Tocopheryl Acetate | 0.50 |
| Nipaguard ® SCP (Clariant) | 1.00 |
| Phenoxyethanol, Sorbitan Caprylate | |

Viscosity: 20,000 mPas; pH: 5.6

Example 5: Soft Caring Shower Cream

| Ingredient | wt % |
|---|---|
| Water | ad 100 |
| Hydroxypropyl Guar (and) Hydroxypropyl Guar Hydroxypropyltrimonium Chloride | 0.15 |
| Citric acid | 2.40 |
| Genapol ® LRO liquid (Clariant) Sodium Laureth Sulfate | 44.80 |
| Glycerin (85%) | 3.50 |
| Lauryl/Myristyl Polyricinoleate & Glycerin | 1.00 |
| Fragrance | 0.20 |
| Trisodium Citrate | 0.30 |
| Sodium Benzoate | 0.30 |
| Potassium Sorbate | 0.30 |
| Perlogen ® SF 3000 (Clariant) Aqua, Glycol Distearate, Laureth-4, Cocamidopropyl Betaine | 2.50 |
| GlucoTain ® liquiFlex (Clariant) Lauroyl/Myristoyl Methyl Glucamide (and) Coco-Betaine | 8.90 |
| Sodium Chloride | q.s. |

Viscosity: 13,300 mPas; pH: 4.5

Example 6: Hydrating Lip Balm

| Ingredient | wt % |
|---|---|
| Castor Oil *Ricinus Communis* (Castor) Seed Oil | ad 100 |
| Plantasens ® Refined Jojoba Oil (Clariant) *Simmondsia Chinensis* (Jojoba) Oil | 5.00 |
| Hydrogenated Poly-1-Decene | 10.00 |
| Lauryl/Myristyl Polyricinoleate & Glycerin | 10.00 |
| Caprylic/Capric Triglyceride | 5.00 |
| Plantasens ® Refined Shea Butter (Clariant) *Butyrospermum Parkii* (Shea Butter) | 5.60 |
| C26-28 Alkyl Dimethicone | 2.25 |
| SilCare ® Silicone 41M65 (Clariant) *Stearyl Dimethicone* | 5.60 |
| *Cera Alba* (Beeswax) | 10.00 |
| *Copernicia Cerifera* (Carnauba) Wax | 4.50 |
| *Euphorbia Cerifera* (Candelilla) Wax | 7.80 |
| Ozokerite | 4.50 |
| Cetyl Palmitate | 5.60 |
| Butylated hydroxytoluene | 0.10 |
| Nipaguard ™ POB (Clariant) Phenoxyethanol (and) Benzoic Acid (and) Piroctone Olamine | 1.00 |

Viscosity: not applicable; pH: not applicable

Example 7: Overnight Mask

| Ingredient | wt % |
|---|---|
| Water | ad 100 |
| Glycerin | 4.00 |
| Beraclay Light Green Kaolin | 4.00 |

-continued

| Ingredient | wt % |
|---|---|
| Lauryl/Myristyl Polyricinoleate & Glycerin | 5.00 |
| Caprylic/Capric Triglyceride | 3.00 |
| Plantasens ® Olive LD (Clariant) Hydrogenated Ethylhexyl Olivate, Hydrogenated Olive Oil Unsaponifiables | 5.00 |
| Plantasens ® Emulsifier HP 30 (Clariant) Glyceryl Stearate, Cetearyl Alcohol, Sodium Stearoyl Lactylate | 3.00 |
| Plantasens ® Emulsifier DGDS (Clariant) Polyglyceryl-2 Distearate | 5.00 |
| Plantasens ® Refined Babassu Butter (Clariant) *Orbignya Oleifera* (Babassu) Seed Oil | 3.00 |
| Plantasens ® Cosmetic Wax A5 (Clariant) Hydrogenated Vegetable Oil | 1.00 |
| Stearic Acid | 1.00 |
| Plantasens ® Olive Active HP (Clariant) *Olea Europaea* (Olive) Oil Unsaponifiables | 3.00 |
| Nipaguard ® EHP (Clariant) Phenoxyethanol (and) Ethylhexylglycerin | 1.00 |
| Tocopheryl Acetate | 0.30 |
| Fragrance | 0.30 |
| Citric Aid | q.s. |

Viscosity: 16,300 mPas; pH: 5.5

Example 8: Deep Nutrition Hand and Foot Cream

| Ingredient | wt % |
|---|---|
| Water | ad 100 |
| Plantasens ® Refined Cocoa Butter (Clariant) *Theobroma Cacao* (Cocoa) Seed Butter | 10.00 |
| Plantasens ® Refined Shea Butter (Clariant) *Butyrospermum Parkii* (Shea Butter) | 5.00 |
| Lauryl/Myristyl Polyricinoleate & Glycerin | 5.00 |
| Plantasens ® Emulsifier HP 30 (Clariant) Glyceryl Stearate, Cetearyl Alcohol, Sodium Stearoyl Lactylate | 5.00 |
| Glycerin | 5.00 |
| Nipaguard ™ POB (Clariant) Phenoxyethanol (and) Benzoic Acid (and) Piroctone Olamine | 1.00 |
| Sodium Hydroxide | q.s. |

Viscosity: 43,000 mPas; pH: 6.0

The invention claimed is:

1. A cosmetic composition for cosmetic treatment of skin, wherein the composition comprises from 0.5 wt % to 10 wt %, based on the total weight of the cosmetic composition, of at least one compound according to Formula (1)

Formula (1)

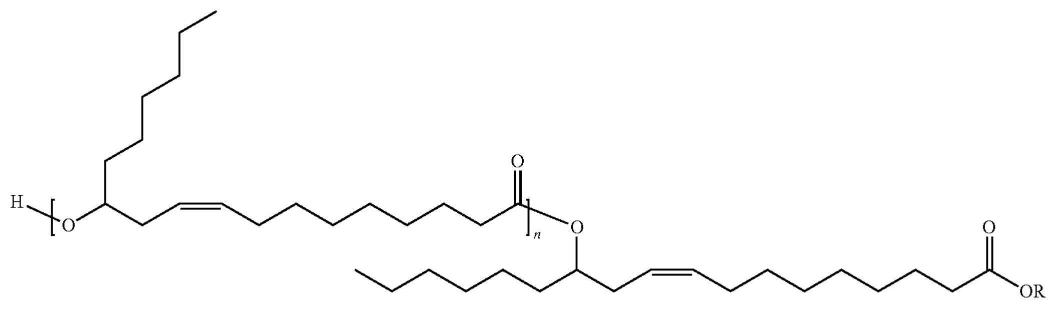

wherein

R is a linear C10-C16-alkyl; and n is selected from 2 to 8; and from 1 wt % to 30 wt %, based on the total weight of the cosmetic composition, of at least one sun protection agent, UV filter, pigment, or a combination thereof, wherein the cosmetic composition is a sunscreen lotion, sun cream, sunscreen gel, sunblock, foundation, primer, concealer, blush, bronzer, blemish balm (BB) cream, highlighter, illuminator, eye shadow, eyeliner, mascara, lipstick, lip gloss, lip stain, lip crayon, day cream, face cream, moisturizer, serum, anti-aging cream, eye cream, hand cream, body lotion, body milk, baby cream, after-shave lotion, pre-shaving cream, anti-acne gel, skin-whitening gel, cellulite treatment, foot cream, deodorant, antiperspirant, insect repellent, body oil, body mousse, or skin conditioner.

2. The cosmetic composition according to claim 1, wherein R is a linear C12-C14-alkyl and n is from 3 to 7.

3. The cosmetic composition according to claim 1, wherein the cosmetic composition comprises from 1 wt % to 5 wt %, based on the total weight of the cosmetic composition, of the at least one compound according to Formula (1).

4. The cosmetic composition according to claim 1, wherein the cosmetic composition comprises from 15 wt % to 30 wt %, based on the total weight of the cosmetic composition, of at least one sun protection agent or UV filter.

5. The cosmetic composition according to claim 1, wherein the cosmetic composition comprises at least one sun protection agent or UV filter selected from the group consisting of 4-aminobenzoic acid, 3-(4'-trimethylammonium)-benzylidene-bornan-2-one-methylsulfate, camphor benzalkonium methosulfate, 3,3,5-trimethyl-cyclohexylsalicylate, 3,3'-(1,4-phenylenedimethine)-bis(7,7-dimethyl-2-oxobicyclo[2.2.1]-heptane-1-methanesulfonic acid), 1-(4-tert-butylphenyl)-3-(4-methoxyphenyl) propane-1,3-dione, 3-(4'-sulfo)-benzylidene-bornan-2-one, 2-cyano-3,3-diphenylacrylic acid-(2-ethylhexyl ester), polymers of N-[2 (and 4)-(2-oxoborn-3-ylidenemethyl)benzyl]-acrylamide, 4-methoxy-cinnamic acid-2-ethylhexyl ester, ethoxylated ethyl-4-aminobenzoate, 4-methoxy-cinnamic acid isoamyl ester, 2,4,6-tris-[p-(2-ethylhexyloxycarbonyl) anilino]-1,3,5-triazine, 2-(2H-benzotriazol-2-yl)-4-methyl-6-(2-methyl-3-(1,3,3,3-tetramethyl-1-(trimethylsilyloxy)-disiloxanyl)-propyl) phenol, 4,4'-[(6-[4-((1,1-dimethylethyl)-aminocarbonyl)phenylamino]-1,3,5-triazin-2,4-yl)diimino]bis-(benzoic acid-2-ethylhexyl ester), benzophenone-3, benzophenone-4 (acid), 3-(4'-methylbenzylidene)-D,L-camphor (4 methylbenzylidene camphor), 3-benzylidene-camphor, salicylic acid-2-ethylhexyl ester, 4-dimethylaminobenzoic acid-2-ethylhexyl ester, hydroxy-4-methoxy-benzophenone-5-sulfonic acid (sulfisobenzonum), 4-isopropylbenzylsalicylate, N,N,N-trimethyl-4-(2-oxoborn-3-ylidenemethyl) anilinium methyl sulfate, homosalate, oxybenzone, 2-phenylbenzimidazole-5-sulfonic acid, octylmethoxycinnamic acid, isopentyl-4-methoxycinnamic acid, isoamyl-p-methoxycinnamic acid, 2,4,6-trianilino-(p-carbo-2'-ethylhexyl-1'-oxy)-1,3,5-triazine (octyl triazone), 2-(2H-benzotriazol-2-yl)-4-methyl-6-(2-methyl-3-(1,3,3,3-tetramethyl-1-(trimethylsilyl)oxy)-disiloxanyl) propyl benzoic acid, 4,4'-((6-(((1,1-dimethylethyl)amino) carbonyl)phenyl)amino)-1,3,5-triazine-2,4-diyl)diimino) bis (2-ethylhexyl ester)benzoic acid, benzylidene-camphor-sulfonic acid, octocrylene, polyacrylamidomethyl-benzylidene-camphor, 2-ethylhexyl salicylate (octyl salicylate), 4-dimethylaminobenzoic acid ethyl-2-hexyl ester (octyl dimethyl PABA), PEG-25 PABA, 2-hydroxy-4-methoxybenzophenone-5-sulfonic acid, 2,2'-bis-(1,4-phenylene)-1H-benzimidazole-4,6-disulfonic acid, (1,3,5)-triazine-2,4-bis ((4-(2-ethylhexyloxy)-2-hydroxy)phenyl)-6-(4-methoxyphenyl), 2-ethylhexyl-2-cyano-3,3-diphenyl-2-propenoate, glyceryl octanoate di-p-methoxycinnamic acid, p-aminobenzoic acid and esters thereof, 4-tert-butyl-4'-methoxydibenzoylmethane, 4-(2 β-glucopyranoxy) propoxy-2-hydroxybenzophenone, methyl-2,5-diisopropylcinnamic acid, cinoxate, dihydroxy-dimethoxybenzophenone, 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl-dimethoxybenzylidene-dioxoimidazolidine propionate, methylene-bis-benzotriazolyl tetramethylbutylphenol, phenyldibenzimidazole tetrasulfonate, bis-ethylhexyloxyphenol-methoxyphenyl-triazine, tetrahydroxybenzophenones, terephthalylidene-dicamphor-sulfonic acid, 2,4,6-tris[4-(2-ethylhexyloxycarbonyl) anilino]-1,3,5-triazine, methyl-bis (trimethylsiloxy) silyl-isopentyl trimethoxycinnamic acid, amyl-p-dimethylaminobenzoate, 2-ethylhexyl-p-dimethylaminobenzoate, isopropyl-p-methoxycinnamic acid/diisopropylcinnamic acid ester, 2-ethylhexyl-p-methoxycinnamic acid, 2-hydroxy-4-methoxybenzophenone, phenylbenzimidazole-sulfonic acid, p-aminobenzoic acid butyl ester, methyl-3-[2,4-bis(methylethyl)phenyl]-2-propenoate, 3-(4-hydroxy-3-methoxyphenyl)-2-propenoic acid, 5-methyl-2-(1-methylethyl)cyclohexanol-2-aminobenzoate, diethylmalonylbenzylidene oxypropene dimethicone, 2,4,6-tris(biphenyl-4-yl)-1,3,5-triazine, tris(2-hydroxyethyl) ammonium 2-hydroxybenzoate, and any salts or hydrates of these.

6. The cosmetic composition according to claim 1, wherein the cosmetic composition comprises from 1 wt % to 20 wt %, based on the total weight of the cosmetic composition, of at least one pigment.

7. The cosmetic composition according to claim 1, wherein the cosmetic composition comprises at least one pigment selected from the group consisting of titanium dioxide, mica-titanium oxide, iron oxides, mica-iron oxide, zinc oxide, silicon oxides, chromium oxides, chalk, ochre, umber, green earth, burnt sienna, graphite, black iron oxide (CI77499), yellow iron oxide (CI77492), red iron oxide (CI77491), brown iron oxide, manganese violet (CI77742), ultramarine (sodium aluminum sulfosilicate, CI 77007, Pigment Blue 29), chromium oxide hydrate (CI77289), Prussian blue (ferric ferrocyanide, CI77510), carmine, mica, silica, bismuth oxychloride, boron nitride, aluminum, aluminum oxide, silicium dioxide, silicates, calcium aluminum borosilicate, calcium sodium borosilicate, magnesium aluminum silicate, sodium magnesium fluorosilicate, tin oxide, aluminum hydroxide, sepia, gamboge, bone charcoal, Cassel brown, indigo, chlorophyll, azo pigments, anthraquinoids, indigoids, dioxazine, quinacridone, phthalocyanine, isoindolinone, perylene, perinone, metal complex, alkali blue, and diketopyrrolopyrrole pigments.

8. The cosmetic composition according to claim 1, wherein the composition comprises at least one pigment with a particle size of from 1 micron to 200 microns.

9. The cosmetic composition according to claim 1, wherein the cosmetic composition is a sunscreen lotion, sun cream, sunscreen gel, or sunblock.

10. A method for cosmetic treatment of skin, wherein the method comprises the step of applying onto the skin a cosmetic composition comprising from 0.5 wt % to 10 wt %, based on the total weight of the cosmetic composition, of at least one compound according to Formula (1)

Formula (1)

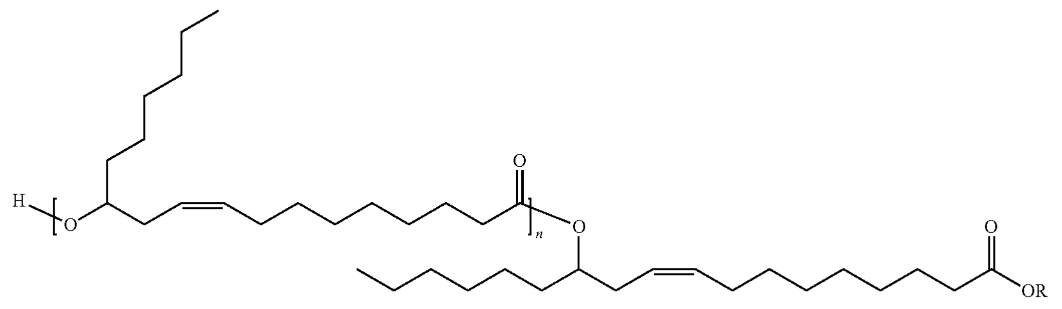

wherein

R is a linear C10-C16-alkyl; and n is selected from 2 to 8; and from 1 wt % to 30 wt %, based on the total weight of the cosmetic composition, of at least one sun protection agent, UV filter, pigment, or a combination thereof.

11. The method according to claim 10, wherein R is a linear C12-C14-alkyl and n is selected from 3 to 7.

12. The method according to claim 10, wherein the cosmetic treatment of skin comprises skin anti-aging treatment, skin anti-wrinkle treatment, UV protection, application of color cosmetics, or any combination thereof.

13. The method according to claim 10, wherein the cosmetic composition comprises from 1 wt % to 5 wt %, based on the total weight of the cosmetic composition, of the at least one compound according to Formula (1); and from 15 wt % to 30 wt %, based on the total weight of the cosmetic composition, of at least one sun protection agent or UV filter; from 1 wt % to 20 wt %, based on the total weight of the cosmetic composition, of at least one pigment; or a combination thereof.

14. The method according to claim 10, wherein the cosmetic composition comprises at least one sun protection agent or UV filter selected from the group consisting of 4-aminobenzoic acid, 3-(4'-trimethylammonium)-benzylidene-bornan-2-one-methylsulfate, camphor benzalkonium methosulfate, 3,3,5-trimethyl-cyclohexylsalicylate, 3,3'-(1,4-phenylenedimethine)-bis(7,7-dimethyl-2-oxobicyclo[2.2.1]-heptane-1-methanesulfonic acid), 1-(4-tert-butylphenyl)-3-(4-methoxyphenyl) propane-1,3-dione, 3-(4'-sulfo)-benzylidene-bornan-2-one, 2-cyano-3,3-diphenylacrylic acid-(2-ethylhexyl ester), polymers of N-[2 (and 4)-(2-oxoborn-3-ylidenemethyl)benzyl]-acrylamide, 4-methoxy-cinnamic acid-2-ethylhexyl ester, ethoxylated ethyl-4-aminobenzoate, 4-methoxy-cinnamic acid isoamyl ester, 2,4,6-tris-[p-(2-ethylhexyloxycarbonyl) anilino]-1,3,5-triazine, 2-(2H-benzotriazol-2-yl)-4-methyl-6-(2-methyl-3-(1,3,3,3-tetramethyl-1-(trimethylsilyloxy)-disiloxanyl)-propyl) phenol, 4,4'-[(6-[4-((1,1-dimethylethyl)-aminocarbonyl)phenylamino]-1,3,5-triazin-2,4-yl)diimino] bis-(benzoic acid-2-ethylhexyl ester), benzophenone-3, benzophenone-4 (acid), 3-(4'-methylbenzylidene)-D,L-camphor (4 methylbenzylidene camphor), 3-benzylidene-camphor, salicylic acid-2-ethylhexyl ester, 4-dimethylaminobenzoic acid-2-ethylhexyl ester, hydroxy-4-methoxy-benzophenone-5-sulfonic acid (sulfisobenzonum), 4-isopropylbenzylsalicylate, N,N,N-trimethyl-4-(2-oxoborn-3-ylidenemethyl) anilinium methyl sulfate, homosalate, oxybenzone, 2-phenylbenzimidazole-5-sulfonic acid, octylmethoxycinnamic acid, isopentyl-4-methoxycinnamic acid, isoamyl-p-methoxycinnamic acid, 2,4,6-trianilino-(p-carbo-2'-ethylhexyl-1'-oxy)-1,3,5-triazine (octyl triazone), 2-(2H-benzotriazol-2-yl)-4-methyl-6-(2-methyl-3-(1,3,3,3-tetramethyl-1-(trimethylsilyl)oxy)-disiloxanyl) propyl benzoic acid, 4,4'-((6-(((1,1-dimethylethyl)amino) carbonyl) phenyl)amino)-1,3,5-triazine-2,4-diyl)diimino) bis(2-ethylhexyl ester)benzoic acid, benzylidene-camphor-sulfonic acid, octocrylene, polyacrylamidomethyl-benzylidene-camphor, 2-ethylhexyl salicylate (octyl salicylate), 4-dimethylaminobenzoic acid ethyl-2-hexyl ester (octyl dimethyl PABA), PEG-25 PABA, 2-hydroxy-4-methoxybenzophenone-5-sulfonic acid, 2,2'-bis-(1,4-phenylene)-1H-benzimidazole-4,6-disulfonic acid, (1,3,5)-triazine-2,4-bis((4-(2-ethylhexyloxy)-2-hydroxy)phenyl)-6-(4-methoxyphenyl), 2-ethylhexyl-2-cyano-3,3-diphenyl-2-propenoate, glyceryl octanoate di-p-methoxycinnamic acid, p-aminobenzoic acid and esters thereof, 4-tert-butyl-4'- methoxydibenzoylmethane, 4-(2 β-glucopyranoxy) propoxy-2-hydroxybenzophenone, methyl-2,5-diisopropylcinnamic acid, cinoxate, dihydroxy-dimethoxybenzophenone, 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl-dimethoxybenzylidene-dioxoimidazolidine propionate, methylene-bis-benzotriazolyl tetramethylbutylphenol, phenyldibenzimidazole tetrasulfonate, bis-ethylhexyloxyphenol-methoxyphenyl-triazine, tetrahydroxybenzophenones, terephthalylidene-dicamphor-sulfonic acid, 2,4,6-tris[4-(2-ethylhexyloxycarbonyl) anilino]-1,3,5-triazine, methyl-bis (trimethylsiloxy) silyl-isopentyl trimethoxycinnamic acid, amyl-p-dimethylaminobenzoate, 2-ethylhexyl-p-dimethylaminobenzoate, isopropyl-p-methoxycinnamic acid/diisopropylcinnamic acid ester, 2-ethylhexyl-p-methoxycinnamic acid, 2-hydroxy-4-methoxybenzophenone, phenylbenzimidazole-sulfonic acid, p-aminobenzoic acid butyl ester, methyl-3-[2,4-bis(methylethyl)phenyl]-2-propenoate, 3-(4-hydroxy-3-methoxyphenyl)-2-propenoic acid, 5-methyl-2-(1-methylethyl)cyclohexanol-2-aminobenzoate, diethylmalonylbenzylidene oxypropene dimethicone, 2,4,6-tris(biphenyl-4-yl)-1,3,5-triazine, tris(2-hydroxyethyl) ammonium 2-hydroxybenzoate, and any salts or hydrates of these.

15. The method according to claim 10, wherein the cosmetic composition comprises at least one pigment selected from the group consisting of titanium dioxide, mica-titanium oxide, iron oxides, mica-iron oxide, zinc oxide, silicon oxides, chromium oxides, chalk, ochre, umber, green earth, burnt sienna, graphite, black iron oxide (CI77499), yellow iron oxide (CI77492), red iron oxide (CI77491), brown iron oxide, manganese violet (CI77742), ultramarine (sodium aluminum sulfosilicate, CI 77007, Pigment Blue 29), chromium oxide hydrate (CI77289), Prussian blue (ferric ferrocyanide, CI77510), carmine, mica, silica, bismuth oxychloride, boron nitride, aluminum, aluminum oxide, silicium dioxide, silicates, calcium aluminum borosilicate, calcium sodium borosilicate, magnesium aluminum silicate, sodium magnesium fluorosilicate, tin oxide, aluminum hydroxide, sepia, gamboge, bone charcoal, Cassel brown, indigo, chlorophyll, azo pigments, anthraquinoids, indigoids, dioxazine, quinacridone, phthalocyanine, isoindolinone, perylene, perinone, metal complex, alkali blue, and diketopyrrolopyrrole pigments.

16. The method according to claim 10, wherein the cosmetic composition is a sunscreen lotion, sun cream, sunscreen gel, sunblock, foundation, primer, concealer, blush, bronzer, blemish balm (BB) cream, highlighter, illuminator, eye shadow, eyeliner, mascara, lipstick, lip gloss, lip stain, lip crayon, day cream, face cream, moisturizer, serum, anti-aging cream, eye cream, hand cream, body lotion, body milk, baby cream, after-shave lotion, pre-shaving cream, anti-acne gel, skin-whitening gel, cellulite treatment, foot cream, deodorant, antiperspirant, insect repellent, body oil, body mousse, skin conditioner, or split end fluid.

* * * * *